US006909971B2

(12) United States Patent
Toivonen et al.

(10) Patent No.: US 6,909,971 B2
(45) Date of Patent: Jun. 21, 2005

(54) METHOD FOR GENE MAPPING FROM CHROMOSOME AND PHENOTYPE DATA

(75) Inventors: Hannu T. T. Toivonen, Helsinki (FI); Päivi Onkamo, Helsinki (FI); Kari Vasko, Helsinki (FI); Vesa Ollikainen, Helsinki (FI); Petteri Sevon, Helsinki (FI); Heikki Mannila, Espoo (FI); Juha Kere, Espoo (FI)

(73) Assignee: Licentia Oy, Helsinki (FI)

( * ) Notice: Subject to any disclaimer, the term of this patent is extended or adjusted under 35 U.S.C. 154(b) by 345 days.

(21) Appl. No.: 09/875,935

(22) Filed: Jun. 8, 2001

(65) Prior Publication Data

US 2003/0032015 A1 Feb. 13, 2003

(51) Int. Cl.[7] .................. G01N 33/48; G01N 33/50; G06F 7/00
(52) U.S. Cl. ...................... 702/19; 702/20; 707/102; 435/6
(58) Field of Search .................. 702/19–20; 707/102; 435/6

(56) References Cited

U.S. PATENT DOCUMENTS

| | | | | |
|---|---|---|---|---|
| 5,851,762 A | * | 12/1998 | Simons | 435/6 |
| 5,981,832 A | * | 11/1999 | Johnson | 800/267 |
| 6,291,182 B1 | * | 9/2001 | Schork et al. | 435/6 |
| 6,537,751 B1 | * | 3/2003 | Cohen et al. | 435/6 |
| 2002/0077775 A1 | * | 6/2002 | Schork et al. | 702/179 |
| 2002/0123058 A1 | * | 9/2002 | Threadgill et al. | 435/6 |

OTHER PUBLICATIONS

Pritchard et al. 2001 American Journal of Human Genetics, 69:1–14.*

H. Toivonen et al., "Data mining applied to linkage disequilibrium mapping", American Journal of Human Genetics, 67, pp133–145, Jun. 9, 2000.

H. Toivonen et al., "Gene mapping by haplotype pattern mining", Proceedings of IEEE International Symposium on Bio–Informatics and Biomedical Engineering, pp99–108, Oct. 10, 2000.

P. Sevon et al., "Mining associations between genetic markers, phenotypes and covariates", Wijsman et al. Genetic Analysis Workshop 12, Genetic Epidemiology 21 (Suppl 1), 2001.

K. Vasko, "Data mining techniques on gene mapping", Closed seminar: "Seminar on Computational Research Methods", Department of Computer Science, University of Helsinki, Sep. 1999 by e–mail.

* cited by examiner

*Primary Examiner*—Mary K. Zeman
(74) *Attorney, Agent, or Firm*—Young & Thompson

(57) ABSTRACT

The present invention relates to a method for gene mapping from chromosome and phenotype data, which utilizes linkage disequilibrium between genetic markers $m_i$, which are polymorphic nucleic acid or protein sequences or strings of single-nucleotide polymorphisms deriving from a chromosomal region. All marker patterns P that satisfy a certain pattern evaluation function e(P) are searched from the data, each marker $m_i$ of the data is scored by a marker score and the location of the gene is predicted as a function of the scores $s(m_i)$ of all the markers $m_i$ in the data.

10 Claims, 23 Drawing Sheets

A. Most strongly disease-associated patterns

| Marker     | 01 | 02 | 03 | 04 | 05 | 06 | 07 | 08 |
|------------|----|----|----|----|----|----|----|----|
| Pattern01  | 4  | 1  | 6  | 6  | 3  | *  | *  | *  |
| Pattern02  | 4  | 1  | 6  | 6  | 3  | 6  | *  | *  |
| Pattern03  | 4  | 1  | 6  | 6  | *  | 6  | *  | *  |
| Pattern04  | 4  | 1  | 6  | *  | 3  | 6  | *  | *  |
| Pattern05  | 4  | 1  | *  | 6  | 3  | *  | *  | *  |
| Pattern06  | 4  | 1  | *  | 6  | 3  | 6  | *  | *  |
| Pattern07  | 4  | *  | 6  | 6  | 3  | *  | *  | *  |
| Pattern08  | 4  | *  | 6  | 6  | 3  | 6  | *  | *  |
| Pattern09  | 4  | *  | 6  | *  | 3  | 6  | *  | *  |
| Pattern10  | *  | 1  | 6  | 6  | *  | *  | *  | *  |
| Pattern11  | *  | 1  | 6  | 6  | 3  | *  | *  | *  |
| Frequency  | 9  | 11 | 11 | 11 | 10 | 6  | 0  | 0  |

FIG. 1A

METHOD FOR GENE MAPPING FROM CHROMOSOME AND PHENOTYPE DATA

FIELD OF THE INVENTION

The present invention relates to a method for gene mapping from chromosome and phenotype data, which utilizes linkage disequilibrium between genetic markers $m_i$, which are polymorphic nucleic acid or protein sequences or strings of single-nucleotide polymorphisms deriving from a chromosomal region.

BACKGROUND OF THE INVENTION

The use of linkage disequilibrium (LD) in detecting disease genes has recently drawn much attention in genetic epidemiology. LD is evaluated with association analysis, which, when applied to disease-gene mapping, requires the comparison of allele or haplotype frequencies between the affected and the control individuals, under the assumption that a reasonable proportion of disease-associated chromosomes has been derived from a common ancestor. Traditional association analysis methods have long been used to test the involvement of candidate genes in diseases and, in special circumstances, to fine-map disease loci found by linkage methods. The testing has mostly been done using simple two-point measures.

Improved statistical methods to detect LD have been presented lately (Terwilliger 1995; Devlin et al. 1996; Lazzeroni 1998; McPeek and Strahs 1999; Service et al. 1999). The newer methods are based on statistical models of LD around a disease susceptibility (DS) gene. Genomic regions—rather than alleles—that are shared among affected individuals, are searched for. The recombination history from the common ancestor to the present day is taken into account with more or less simplified statistical models. The power of these methods, as well as their ability to localize the correct position of the DS gene, has been shown to be better than that of traditional methods. Some of the models are robust to high levels of etiologic heterogeneity (McPeek and Strahs 1999; Service et al. 1999). However, the methods contain assumptions about the inheritance model of the disease and the structure of the survey population, and the effects of violations of these assumptions in the real data are not known. In addition, they can only consider association of one region at a time. Thus, they are currently best suited for fine mapping, rather than complex disease mapping or genome screening. The methods also tend to be computationally heavy.

SUMMARY OF THE INVENTION

The object of the present invention is to provide a model-free and computationally effective method, which overcomes the above mentioned drawbacks. This object is achieved in accordance of the invention by the method for gene mapping from chromosome and phenotype data, which utilizes linkage disequilibrium between genetic markers $m_i$, which are polymorphic nucleic acid or protein sequences or strings of single-nucleotide polymorphisms deriving from a chromosomal region, wherein i) all marker patterns P that satisfy a pattern evaluation function e(P) are searched from the data, wherein
   a. the marker patterns are expressions involving the genetic markers and their alleles and zero or more of the following: individual covariates, environmental variables and auxiliary phenotypes; and
   b. the pattern evaluation function e(P) involves some statistical measure of the association between the marker pattern P and the phenotype being studied, ii) each marker $m_i$ of the data is scored by a marker score $s(m_i)$, which is a function of the set $S_i$ defined as the set of marker patterns overlapping the marker $m_i$ and satisfying the pattern evaluation function e as defined in step (i), and the location of the gene is predicted as a function of the scores $s(m_i)$ of all the markers $m_i$ in the data and is based on maximizing the score if the scoring function is designed to give higher scores closer to the gene, and on minimizing the score if the scoring function is designed to give lower scores closer to the gene, as is the case for instance when the scores $s(m_i)$ are marker-wise p values.

A computer-readable data storage medium according to the invention has computer-executable program code stored thereon, said executable program code being operative to perform a method of any embodiments of the invention when executed on a computer.

A computer system according to the invention is programmed to perform the method of any embodiments of the invention.

DETAILED DESCRIPTION OF THE INVENTION

Figure 1B:
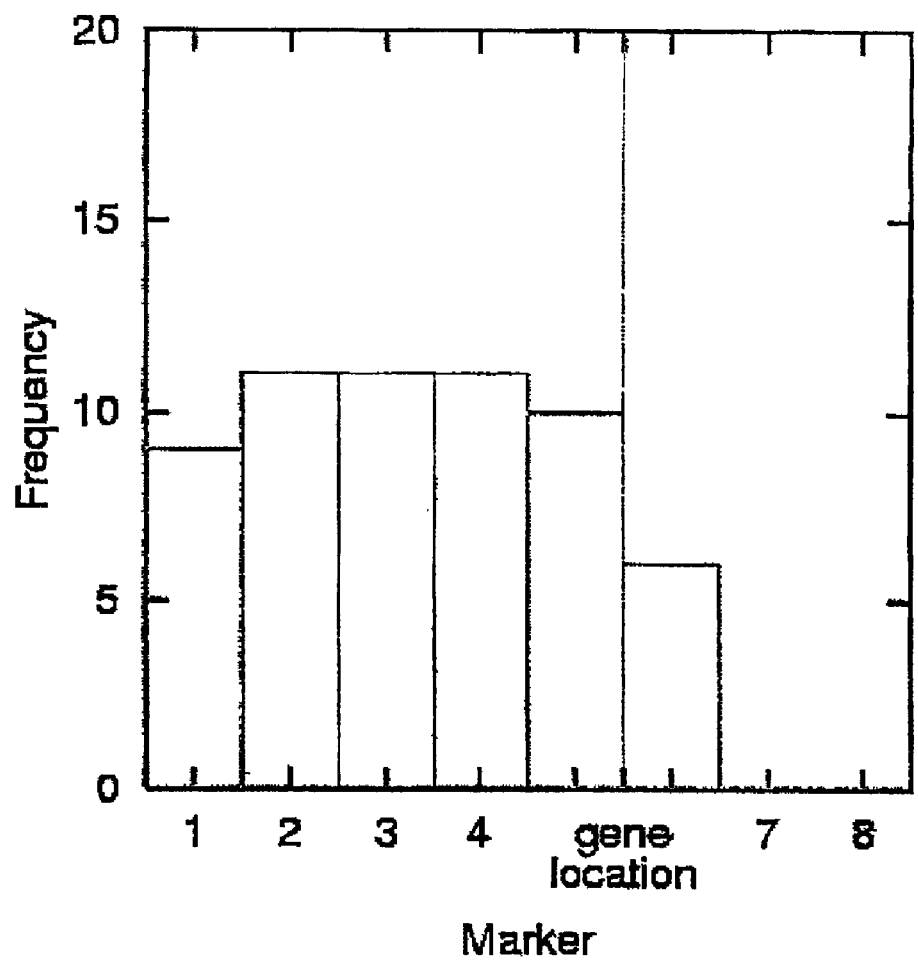
FIG. 1. A. Examples of strongly disease-associated haplotype patterns discovered in a data set with A=10%, only the first 8 markers of 101 are shown. B. Corresponding marker frequencies ("Don't care" symbols (*) in gaps are included in marker frequencies). C. Marker frequencies in the same data set with all strongly disease-associated haplotype patterns. D. Plot of the true versus the predicted locations of the disease susceptibility (DS) gene for 100 data sets (A=10%).

The object of the present invention is to provide a method for gene mapping from chromosome and phenotype data, which utilizes linkage disequilibrium between genetic markers $m_i$, which are polymorphic nucleic acid or protein sequences or strings of single-nucleotide polymorphisms deriving from a chromosomal region.

The chromosome data may consist of either haplotypes or genotypes. The phenotype being studied may also be a combination of several phenotypes.

The method according to the invention, also named as haplotype pattern mining (HPM), uses data mining methods in LD-based gene mapping. The method uses haplotypes or genotypes as input; they can be obtained, for example, with GENEHUNTER (Kruglyak et al. 1996). In diseases with reasonable genetic contribution, affected individuals are likely to have higher frequencies of associated marker alleles near the DS gene than control individuals. Combinations of marker alleles which are more frequent in disease-associated chromosomes than in control chromosomes, are searched for in the data, without assumptions about the mode of inheritance of the disease. These combinations, marker patterns or haplotype patterns, are sorted by the strength of their association to the disease, and the resulting list of marker or haplotype patterns is used in localizing the DS gene. Terms marker patterns and haplotype patterns are both used in this text. Term "marker pattern" includes also "haplotype pattern". However, even if only "haplotype pattern" is mentioned in connection with any steps of the method of the invention, it should be noted that the same details apply also for "marker pattern".

The method according to the present invention is an algorithm-based extension of traditional association analysis. It works with a nonparametric statistical model and without any genetic models. The localization power of the method of the invention is high, even with weak associations—for example, when disease-associated haplotypes are found in only 5%–10% of disease-associated chromosomes at realistic sample sizes (100–200 affected individuals) with either microsatellite or single-nucleotide polymorphism (SNP) data. The method is robust to mutations as well as to missing and erroneous data. Since HPM can handle high degrees of etiologic heterogeneity, it can be successful in complex disease mapping.

LD, the nonrandom association of marker alleles and haplotypes to the disease, is likely to be strongest around the DS gene; consequently the locus is likely to be where most of the strongest associations are. In the HPM method according to the invention, we search for shared, flexible haplotypes that may contain gaps and find out which ones are strongly associated to the disease status. We then use a non-parametric model for predicting the DS locus, on the basis of the locations of the haplotypes. Permutation tests can be used to contrast the results against the null hypothesis that there is no gene effect.

Marker or Haplotype Patterns and Disease Association

We examine linkage disequilibrium by looking for marker or haplotype patterns that consist of a set of nearby markers, not necessarily consecutive ones. Given a marker map M with k markers $m_1, \ldots, m_k$, a "marker pattern" or "haplotype pattern" P on M is defined as a vector $(p_1, \ldots, p_k)$, where each $p_i$ is either an allele of marker $m_i$ or the "don't care" symbol (*). The haplotype pattern P occurs in a given haplotype vector (chromosome) $H=(h_1, \ldots, h_k)$ if $p_i=h_i$ or $p_i=*$ for all i,1 i k. For example, consider a marker map of 10 markers. The vector $P_1=(*, 2, 5, *, 3, *, *, *, *, *)$, where 1, 2, 3, ... are marker alleles, is an example of a haplotype pattern. This pattern occurs, for instance, in a chromosome with haplotype (4, 2, 5, 1, 3, 2, 6, 4, 5, 3).

Our goal is to search for haplotype patterns that roughly correspond to haplotypes identical by descent in the disease-associated chromosomes. In doing this, there are two major issues with respect to the shapes of haplotype patterns: the genetic length of the significant part of the patterns, and gaps. We define the "(genetic) length" of a haplotype pattern $P=(p_1, \ldots, p_k)$ as the maximum distance, in Morgans, between any two markers $m_i, m_j$ with $p_i \neq * \neq p_j$. Searching for haplotype patterns of arbitrary length hardly makes sense; it is unlikely that genetically extremely long patterns will be discovered, at least not in significant numbers. Consequently, when haplotype patterns are searched for, the maximum length of patterns to be considered can be constrained with an optional pattern-search parameter to the HPM method.

We allow for gaps in the marker patterns, since mutations, errors, missing data, and recombinations can corrupt continuous haplotypes. Marker mutations and errors typically cause very short gaps only. Missing information can span several consecutive markers, depending on the data collection scheme. Longer gaps can be introduced by double recombinations which, however, are rare on genetically short distances. In the HPM method, the maximum number and maximum length of gaps can be controlled with pattern search parameters.

Mining Disease-Associated Haplotype Patterns

All marker patterns P that satisfy a pattern evaluation function e(P) are searched from the data in the step (i) of the method of the invention. The pattern evaluation function e(P) involves some statistical measure of the association between the marker pattern P and the phenotype being studied. In step (ii), each marker $m_i$ of the data is scored by a marker score $s(m_i)$, which is a function of the set $S_i$ defined as the set of marker patterns overlapping the marker $m_i$ and satisfying the pattern evaluation function e as defined in step (i).

In step (i), let U be the universe of marker patterns considered in the study. The output S of this phase is the set of those marker patterns that satisfy e, i.e., S={P∈U|e(P) is true}.

In step (ii), for each marker $m_i$ in the data, let $S_i$={P∈U|P makes a reference to $m_i$, or to a marker to the left of and to a marker to the right of $m_i$} be the set of patterns in S that overlap with the marker $m_i$. In this phase each marker $m_i$ is scored as a function of $S_i$ and the result is $s(m_i)$.

In step (iii), the location of the gene is predicted as a function of the scores $s(m_i)$ of all the markers $m_i$ in the data. This function returns an area where the gene is likely to be. The area can be contiguous or fragmented, and it can be point as a special case.

The marker or haplotype patterns P can be searched by an algorithm developed by the inventors for this purpose or by the levelwise search method described in [Heikki Mannila and Hannu Toivonen: Levelwise search and borders of theories in knowledge discovery, *Data Mining and Knowledge Discovery* 1(3): 241–258, November 1997]. Preferred algorithms are given in the following.

Version 1 of the Algorithm for Marker Pattern Searching

The following algorithm is a simple, generic, and efficient way to implement step (i). of the method according to the invention. It is based on depth first search in the space of patterns, a standard procedure in computer science. A prerequisite is that there is a suitable generalization relation for the patterns, such that if a pattern satisfies the evaluation function, then all more general patterns also satisfy it.

Input set U of marker patterns evaluation function e(P) for patterns P in U (generalization) relation < for patterns in U where the function e and the relation < are such that if e(P) is true and P'<P, then e(P') is also true Output set S={P∈U|e(P) is true} of patterns

```
Method
1. S := { }
2. // Initialize the set of evaluated patterns:
3. E := { }
4. // Start with the most general patterns:
5. Gen := {P in U|there is no P' in U, P' != P, such that P' <P}
6. // Recursively evaluate patterns in a depth first order:
7. foreach P ∈ Gen {evaluatePatterns(P) }
8. end;
9. procedure evaluatePatterns(P) {
10.     insert P into the set E
11.     if e(P) = true then {
12.         insert P into set S
13.         // Find all specializations of P that have not been tested yet, and
14.         // evaluate them recursively:
15.         Spec := {P' in U-E |P < P', P' != P, and there is no P" in U-E, P" != P
16.             and P" != P', with P < P" < P'};
17.         foreach P' in Spec {evaluatePatterns(P'); }
18.     }
19.}
```

Version 2 of the Algorithm for Marker Pattern Searching

The following algorithm is a simple, generic, and efficient way to implement step (i). of the method according to the invention. It is based on depth first search in the space of patterns, a standard procedure in computer science. It approximates the exact answer by ignoring infrequent and therefore statistically less important patterns.

Define an auxiliary evaluation function ae(P) which is true if and only if the frequency of pattern P exceeds a given threshold x, (how to specify the threshold is discussed elsewhere) and replace the original evaluation function e(P) by function e'(P) defined as e'(P)=true if and only if e(P) is true and ae(P) is true. This refinement prunes patterns that satisfy e but are no more frequent than x. Such infrequent patterns are statistically not relevant, and therefore little information is lost when they are ignored. Now a suitable generalization relation is obtained from logical implication based on the pattern syntax: P<P' if and only if P'->P.

The algorithm uses the generalization relation based on logical implication to structure the search space, and the auxiliary function ae to prune the search space. All patterns satisfying ae are searched for, but only those also satisfying e are output.

Input set U of marker patterns evaluation function e(P) for patterns P in U frequency threshold x Output set S={P in U|e(P) and ae(P) is true} of patterns, where ae(P) is true if and only if the frequency of pattern P exceeds a given threshold x

```
Method
20. S := { }
21. // Initialize the set of evaluated patterns:
22. E := { }
23. // Start with the most general patterns:
24. Gen := {P in U|there is no P' in U, P' != P, such that P' <P}
25. // Recursively evaluate patterns in a depth first order:
26. foreach P ∈ Gen {evaluatePatterns(P) }
27. end;
28. procedure evaluatePatterns(P) {
29.     insert P into the set E
30.     if e(P) = true then {
31.         insert P into set S
32.         // Find all specializations of P that have not been tested yet, and
33.         // evaluate them recursively:
34.         Spec := {P' in U-E |P < P', P' != P, and there is no P" in U-E, P" != P
35.             and P" != P', with P < P" < P'};
36.         foreach P' in Spec {evaluatePatterns(P'); }
37.     }
38. }
```

Version 3 of the Algorithm for Marker Pattern Searching

When phenotype being studied is qualitative and the pattern evaluation function e(P) has the form e(P)=true if and only if e'(P)>x, where e'(P) is the (signed) association measure $\chi^2$ and x is a user specified minimum value, which is chosen so that the sizes of $S_i$ are large enough, such as 20, to give statistically sufficiently reliable estimates for the gene locus, the following algorithm is a simple, generic, and efficient way to implement step (i). of the method according to the invention. It is based on depth-first search in the syntactic space of patterns. It derives a lower bound lb for pattern frequency from the given lower bound x for chi-squared test, and users lb to prune the search.

Input
  marker map $M=(m_1, \ldots, m_k)$
  phenotype vector $Y=(Y_1, \ldots, Y_n)$
  haplotype matrix H of size n*k
  association threshold x for chi-squared test
  maximum pattern length l
  maximum number of gaps g
  maximum gap size s
Output
  set S={P in U|e(P) is true} of patterns,
    where U consists of patterns on M that consist of marker-allele assignments and that adhere to parameters l, g, and i, and
    where e(P) is true if and only if chi-squared test on P using haplotype matrix H and phenotypes Y exceeds the given threshold x

```
Method
39. S := { }
40. // Number of case and control chromosomes:
41. piA := number of disease-associated chromosomes;
42. piC := number of control chromosomes;
43. pi := piA + piC
44. // A lower bound for pattern frequency:
45. lb := piA * pi * x/(piC * pi + piA * x)
46. // Variable for iterating over different patterns:
47. P = (p1, ..., pk) := ('*', ..., '*')
48. for i := 1 to k {
49.     // alleles(m_i) is the set of alleles of the i:th marker
50.     foreach a in alleles(m_i) {
51.         p_i := a
52.         // Test pattern P and all its extensions:
53.         checkPatterns(P, i, i, 0, 0)
54.         // Reset p_i:
55.         p_i := '*'
56.     }
57. }
58. end
59. // Test haplotype pattern P and all patterns that can be generated by extending P
60. // from the right:
61. procedure checkPatterns(P, start, i, nr_of_gaps, gap_length) {
62.     // Output strongly associated patterns
63.     if chi-squared(P, M, H, Y) >= x and p_i != '*' then insert P into set S
64.     // Return if extended patterns would be too long:
65.     if i = k or i+1-start > l then return
66.     // Return if extended patterns can not be strongly disease-associated:
67.     if frequency of P in disease-associated chromosomes is less than lb
68.     then return;
69.     // Create and test legal extensions of current pattern P (3 cases):
70.     // 1. Give marker i+1 all possible values:
71.     foreach a in alleles(m_i+1) {
```

```
72.        p_i+1:= a
73.        checkPatterns (P, start, i+1, nr_of_gaps, 0)
74.      }
75.      // 2. Introduce a new gap starting at marker i+1:
76.      if p_i≠ '*' and _nr_of_gaps < g and s ≧ then {
77.        p_i+1: '*'
78.        checkPatterns (P, start, i+1, nr_of_gaps+1, 1)
79.      }
80.      // 3. Extend the current gap over marker i+1:
81.      if p_i = '*' and gap_length < s then {
82.        p_i+1 := '*'
83.        checkPatterns (P, start, i+1, nr_of_gaps, gap_length+1)
84.      }
85.      // Before returning, reset p_i+1:
86.      p_i+1 := '*'
87.      return
88. }
```

Version 4 of the Algorithm for Marker Pattern Searching

The following algorithm is a simple, generic, and efficient way to implement step (i). of the method according to the invention. It is based on the levelwise search method described in [Heikki Mannila and Hannu Toivonen: Levelwise search and borders of theories in knowledge discovery, *Data Mining and Knowledge Discovery* 1(3): 241–258, November 1997].

Input set U of marker patterns evaluation function e(P) for patterns P in U (generalization) relation < for patterns in U, where the function e and the relation < are such that if e(P) is true and P'<P, then e(P') is also true Output set S={P in U|e(P) is true} of patterns Definitions function Lgg: U->$2^U$, Lgg(P)={P' in U|P>P' and P'!=P and there is no P" in U such that P!=P"!=P' and P>P">P'}, the set of least general generalizations of pattern P.

function Lss: U->$2^U$, Lss(P)={P' in U|P<P' and P'!=P and there is no P" in U such that P!=P"!=P' and P<P"<P'}, the set of least special specializations of pattern P.

Version 5 of the Algorithm for Marker Pattern Searching

This is the levelwise search version of the algorithm 2.

Input set U of marker patterns evaluation function e(P) for patterns P in U frequency threshold x Output set S={P in U|e(P) and ae(P) is true} of patterns, where ae(P) is true if and only if the frequency of pattern P exceeds a given threshold x Definitions function Lgg: U->$2^U$, Lgg(P)={P' in U|P->P' and P'!=P and there is no P" in U such that P!=P"!=P' and P->P"->P'}, the set of least general generalizations of pattern P.

function Lss: U->$2^U$, Lss(P)={P' in U|P'->P and P'!=P and there is no P" in U such that P!=P"!=P' and P'->P"->P}, the set of least special specializations of pattern P.

```
Method
89. S : = { }
90. Q : = { }
91. // Start with the most general patterns:
92. F : = {P in U | there is no P' in U, P' != P, such that P' < P };
93. while F !={} {
94.      //Evaluate the candidate patterns:
95.      foreach P in F {
96.        if e(P) true then insert P into set S
97.        else remove P from set F
98.      }
99.      Q : = Q union F
100.           // Generate a new set of candidate patterns:
101.           C : = {}
102.           foreach P in F {
103.             C : = C union {P'in U | P'in Lss(P) and for all P" in Lgg(P'):
104.                 P" in Q }
105.      }
106.    F : = C
107. }
108.           end
```

```
Method
109. S : = { }
110. Q : = { }
111. // Start with the most general patterns:
112. F := {P in U | there is no P' in U, P' != P, such that P -> P' };
113. while F != {} {
114.        // Evaluate the candidate patterns:
115.        foreach P in F {
116.            if ae(P) = true then {
117.                if e(P) = true then insert P into set S
118.            }
119.            else remove P from set F
120.        }
121.        Q : = Q union F
122.        // Generate a new set of candidate patterns:
123.        C : = {}
124.        for each P in F {
125.            C : = C union { P' in U | P' in Lss(P) and for all P" in Lgg(P'):
126.                P" in Q }
127.        }
128.        F : = C
129. }
130. end
```

The phenotype being studied may be qualitative, for example disease is present or disease is absent. In that case, the pattern evaluation function e(P) may have the form e(P)=true if and only if e'(P)>x, where e'(P) is the (signed) association measure $\chi^2$ and x is a user specified minimum value, which is chosen so that the sizes of $S_i$ are large enough, such as 20, to give statistically sufficiently reliable estimates for the gene locus and the $s(m_i)$ of marker $m_i$ is the size of $S_i$, also called marker-wise pattern frequency of $m_i$ and denoted by $f(m_i)$.

As mentioned above, the (signed) $\chi^2$ is a measure of marker-disease association. A signed version of the measure is used in order to discriminate disease association from control association. The signed $\chi^2$ measure $\pm\chi^2(P)$ of a haplotype pattern P is positive if P is more frequent in cases than in controls, and negative otherwise. Given a "(positive) association threshold" x, we say that P is "strongly associated" with the disease if $\pm\chi^2(P)$ x.

The first part of the HPM method can be described as follows. Given the data—markers M, haplotypes H, and phenotypes Y—the task is to output all haplotype patterns P that are strongly associated with the disease status for a given value of the association threshold x. We denote the collection of all such haplotype patterns by S—that is, S={P is a haplotype pattern on M|$\pm\chi^2(P)$ x}. If pattern parameters are specified—a maximum genetic length, a maximum number of gaps, or a maximum length for gaps—the task is refined by requiring that these additional restrictions are also fulfilled.

The signed $\chi^2$ value is calculated from a 2×2 contingency table, where the rows correspond to the trait-association statuses of the chromosomes, and the columns correspond to the presence and absence of the haplotype pattern. The value of $\chi^2$ statistic is computed normally, and a negative sign is attached, if the relative frequency of the haplotype pattern among the control chromosomes is higher than that of the trait-associated chromosomes.

The first observation in solving the pattern-mining task is that given an association threshold x, a lower bound can be derived for the frequency of strongly associated haplotype patterns as follows.

Given a 2×2 contingency table of the numbers of disease-associated (A) and control (C) chromosomes either matching a pattern (P) or not (N), the $\chi^2$ test statistic for the disease association of the pattern is defined by $$\frac{(\pi_{AP} \cdot \pi_{CN} - \pi_{AN} \cdot \pi_{CP})^2 \cdot \pi}{\pi_A \cdot \pi_C \cdot \pi_P \cdot \pi_N},$$

where $\pi_{ij}$ is the number of chromosomes with properties i and j, $\pi_i$ the number of chromosomes with property i, and $\pi$ the total number of chromosomes. Given the number of disease-associated chromosomes ($\pi_A$), the number of control chromosomes ($\pi_C$), and a lower bound x for the test statistic, we can derive a lower bound for the pattern frequency among the disease-associated chromosomes ($\pi_{AP}$) as follows. Assuming the pattern is disease-associated, we have $\pi_{AP} \pi_{CN} > \pi_{AN} \pi_{CP}$. The test statistic is maximized when $\pi_{CP}=0$, implying $\pi_{AP}=\pi_P$ and $\pi_{CN}=\pi_C$. Then $$\frac{(\pi_{AP} \cdot \pi_{CN} - \pi_{AN} \cdot \pi_{CP})^2 \cdot \pi}{\pi_A \cdot \pi_C \cdot \pi_P \cdot \pi_N} = \frac{(\pi_{AP} \cdot \pi_C)^2 \cdot \pi}{\pi_A \cdot \pi_C \cdot \pi_{AP} \cdot (\pi - \pi_P)} = \frac{\pi_{AP} \cdot \pi_C \cdot \pi}{\pi_A \cdot (\pi - \pi_{AP})}$$

and $$\frac{\pi_{AP} \cdot \pi_C \cdot \pi}{\pi_A \cdot (\pi - \pi_{AP})} \geq x \Rightarrow \pi_{AP} \geq \frac{\pi_A \cdot \pi \cdot x}{\pi_C \cdot \pi + \pi_A \cdot x}.$$

The situation is symmetric for protective haplotypes, and the lower bound for $\pi_{CP}$ is obtained by simply swapping $\pi_A$ and $\pi_C$ in the above result. If disease-associated and protective haplotypes are searched for at the same time, the smaller of $\pi_{AP}$ and $\pi_{CP}$ can be used as a lower bound for $\pi_P$, making the implementation slightly simpler.

On another hand, given such a frequency threshold, all patterns exceeding the threshold can be enumerated efficiently with data-mining algorithms or a standard depth-first search method. An algorithm that first finds all haplotype patterns whose frequency exceeds the computed lower bound and then evaluates the association measure on them, is guaranteed to find the exact set of strongly disease-associated patterns.

The approach is suitable for finding protective haplotypes, by considering patterns P with $\pm\chi^2(P)$ −x. The derivation of the lower bound for the frequency among controls is identical to the case above. Obviously, both disease-associated and protective haplotypes can be found when $|\pm\chi^2(P)|$ x.

In an other embodiment according to the invention, the phenotype being studied may be, in addition to qualitative, also quantitative, for example a measured blood concentration of a substance has a certain value. In that case, the pattern evaluation function e(P) may have the form e(P)= true if and only if e'(P)>x, where e'(P) is the absolute frequency of pattern P in the data and x is a user-specified value, which is chosen so that the sizes of $S_i$ are large enough, such as 20, to give statistically sufficiently reliable estimates for the gene locus. In this embodiment, the statistical strength of the method may be still increased.

A linear model is of form $Y=\beta_1 X_1 + \ldots + \beta_k X_k + \alpha Z + \beta_0$, where the dependent variable Y is a quantitative phenotype, $X_1$ through $X_k$ are covariates, such as environmental factors, and Z is a dummy variable for the occurrence of the haplotype pattern. Firstly, the coefficients $\alpha$ and $\beta^*$ are adjusted for best fit. Secondly, the significance of Z as a covariate is assessed using a t test. If the phenotype is dichotomous, then the logit transformation can be applied.

Marker Scoring in the Case of Qualitative Phenotype Being Studied

Haplotype patterns close to the DS locus are likely to have stronger association than haplotypes further away; consequently the locus is likely to be where most of the strongest associations are. In one embodiment according to the invention, the marker score $s(m_i)$ is defined as the marker frequency $f(m_i)$ of marker $m_i$ (with respect to M,H,Y,x) as the number of patterns that contain marker $m_i$, possibly mi in a gap: $f(m_i)=|\{P=(p_1, \ldots, p_k) \in S|$ there exist t i and u i such that $p_t * p_u\}|$. The idea is that each haplotype pattern roughly corresponds to a continuous chromosomal region, potentially identical by descent, where gaps allow for corruption of marker data. While markers within gaps are not used in measuring the disease association of the pattern, the whole chromosomal region of the pattern is thought to be relevant.

Marker Scoring in the Case of Qualitative or Quantitative Phenotype Being Studied In order to derive the score $s(m_i)$, the p value (statistical significance) of each marker pattern P in determining the phenotype being studied is evaluated, and the score $s(m_i)$ is the distance between the observed p value distribution of patterns in $S_i$ and the uniform distribution, defined as average of $(p_i-q_i)\log(p_i/q_i)$ over all i=1 ... n, where n is the number of haplotype patterns in $S_i$, $p_i$ is the ith smallest p value in $S_i$, and $q_i$ is the expectation of the ith smallest p value, if the p values were randomly drawn from the uniform distribution.

Gene Localization

The location of the gene, predicted as a function of the scores $s(m_i)$ and based on maximizing or minimizing the score, is predicted to the location of the marker $m_i$ that maximizes or minimizes the marker score $s(m_i)$, or the combination of most probable intervals for containing the trait-susceptibility locus that covers at most the desired proportion t (t∈{0,100%}) of the original region obtained by taking all such points in the studied chromosomal region whose nearest marker is within the k best scoring markers, where k is selected such that the resulting area has length at most t times the length of the studied region, and where k is maximal such value, or those points in the studied chromosomal region whose nearest marker scores at least y or at most y, where y is scoring function dependent and is selected so that the probability of the gene being close to the marker is sufficiently large.

The location of the gene may also be determined by expert investigation of the marker scores or their visualization e.g. as a curve.

Permutation Tests

More information about the significance of the observed scores may be obtained by permutation tests. The results obtained by considering the marker frequencies or the linear model, as explained earlier, can be contrasted against the null hypothesis that all the chromosomes are drawn from the same distribution; that is, there is no gene effect in the disease status. We propose to permute randomly the status fields of the chromosomes, keeping the proportions of affected and control chromosomes constant, in a fashion similar to the method of Churchill and Doerge (1994). We approximate marker-wise p values using permutations and then predict the DS gene to be in the vicinity of the marker with the smallest empirical p value. Consecutive markers are dependent, and thus a large number of mutually dependent p values are produced. This is not a problem, since we do not use the p values for hypothesis testing, but only for ranking markers.

Marker-wise p values are used to re-score markers by their statistical unexpectedness. The test is carried out as follows: The phenotypes of the chromosomes are randomly shuffled a number (thousands) of times. The scores are re-calculated for each permutation in turn. Marker-wise p value $p(m_i)$ is the proportion of such permutation scores for marker $m_i$ that are larger than or equal to the non-permuted score.

Each score $s(m_i)$ is the refined by replacing it by the marker-wise p value $p(m_i)$ of the score $s(m_i)$.

Searching Several Genes

Several genes may be searched for simultaneously by using marker patterns that refer to several potential gene loci at the same time.

EXAMPLES

Certain embodiments and results of the present invention are described in the following non-limiting examples.

Example 1

Simulated Data Sets

We evaluated the performance of the proposed HPM method with simulated data sets that correspond to a recently founded, relatively isolated founder subpopulation. Simulation of a population isolate was chosen, since it is recommended as the study population for LD studies. However, the method can be applied to any population that is suitable for LD analysis, since no assumptions are made about the population structure.

An isolated founder population which grows from the initial size of 300 to about 100,000 individuals in 500 years was simulated. Each individual was assigned to have one pair of homologous chromosomes. The genetic length of the chromosomes was 100 cM for both males and females. No chiasma interference was modeled. In all microsatellite-marker simulations, the information content (PIC) of each marker was fixed at 0.7, and the markers were spaced at intervals of 1 cM. In the SNP data, marker loci were simulated with a density of 3 markers per 1 cM of chromosome. The allele frequency was set to 0.5, and the PIC was thus fixed at 0.375.

We used a dominant disease model with a high phenocopy rate in our experiments. The sample size was 400 chromosomes (200 individuals), of which 200 were control chromosomes. This relatively small sample size was used to study the performance of the method in realistic situations. In the affected sample the proportion of mutation-carrying chromosomes, denoted by A, was either 2.5%, 5%, 7.5%, or 10%, corresponding to over-all relative risks of $\lambda=1.2$, $\lambda=1.7$, $\lambda=2.7$, and $\lambda=4.1$, respectively, for first-degree relatives. These low IBD and $\lambda$ values were chosen, as the higher are easy to handle with existing methods. We ignored marker mutations in the simulation procedure, but compensated for this by evaluating the performance in presence of missing and corrupted data. Both were introduced by removing or changing alleles randomly and independently. The amount of missing data varied between 0% and 20%, and the fraction of corrupted alleles between 0% and 10%.

We used the Populus simulator package (V. Ollikainen, H. Mannila, R. Kilpikari, M. Koivisto, H. Kärkkäinen, M. Mäkelä, P. Onkamo, S. Smolander, and J. Kere, unpublished data), as explained below, to obtain artificial data sets for the analyses.

The package consists of a pedigree generator and a chromosome simulator, and enables creation of data sets with realistic linkage disequilibrium.

The population generator of Populus simulator package was used to generate 100 artificial pedigrees that correspond to the population-specific demographical parameters in the history (Table 1). Each of the resulting 100 very large pedigrees contains all individuals that have lived in the population since the date of foundation. Then the chromosome simulator of the Populus package was used to simulate the inheritance of pairs of homologous chromosomes within each large pedigree. Finally, when the inheritance histories of all chromosomal segments were available, markers were assigned to the original founder individuals, which allowed us to unequivocally determine the alleles of each artificial person in the current population.

TABLE 1

Parameters Used to Simulate Populations

| Parameter | Value[a] | | |
|---|---|---|---|
| Probability of marriage, male (ages 18–32 years) | .9 | | |
| Probability of marriage, female (ages 17–31 years) | .9 | | |
| Maximum age at pregnancy (years) | 44 | | |
| Initial age structure: | | | |
| 0 years | .03 | | |
| 1 years | .12 | | |
| 2–5 years | .15 | | |
| 6–15 years | .24 | | |
| 16–45 years | .40 | | |
| 46–75 years | .06 | | |
| Proportion of descendants in initial population (by age): | | | |
| 0–15 years | .5 | | |
| 15–20 years | .5 | .3[b] | |
| 20–30 years | .3 | | .2 |
| 30–50 years | .2 | 0 | |
| 50–75 years | 0 | | |
| Starting year | 1500 | | |
| Initial population size (in 1500) | 300 | | |

TABLE 1-continued

Parameters Used to Simulate Populations

| Parameter | Value[a] | | |
|---|---|---|---|
| Expected no. of children, by time period: | | | |
| 1500–1775 | 5.5 | | |
| 1776–1915 | 5.5 | 4.0 | |
| 1916–2000 | 4.0 | 1.6 | |
| Immigration rate | 0 | | |
| Probability of death (function of birth year and age): | | | |
| 1400–1750: | | | |
| 0 years | .22 | | |
| 1–10 years | .10 | | |
| 11–25 years | .10 | | |
| 26–35 years | .08 | | |
| 36–45 years | .15 | | |
| 46–65 years | .25 | | |
| 66–85 years | .10 | | |
| 1751–1900: | | | |
| 0 years | .15 | | |
| 1–10 years | .085 | | |
| 11–25 years | .085 | | |
| 26–35 years | .18 | | |
| 36–40 years | .1 | | |
| 41–45 years | .05 | | |
| 46–65 years | .2 | | |
| 66–85 years | .15 | | |
| 1901–2000: | | | |
| 0 years | .05 | | |
| 1–5 years | .035 | | |
| 6–15 years | .005 | | |
| 16–35 years | .125 | | |
| 36–65 years | .18 | | |
| 66–85 years | .605 | | |

[a]Parameter values are functions of year and age of each individual.
[b]An arrow denotes linear interpolation within the given ranges.

In the simulations we assigned a single pair of chromosomes to each founder, and set the genetic length of the chromosomes to 100 cM for both males and females. The meiosis was modeled under the assumption of no chiasma interference, which corresponds to Haldane's model.

In our simulations, we used the Finnish Kainuu subpopulation as our model population. We defined the population to have been founded 500 years ago by a group of 300 individuals, where the total number of independent founders was 198, and the remaining 102 initial settlers were their descendants. This serves as a conservative approximation, since the isolate is estimated to be founded in those times by a relatively small group of individuals migrating from the south. For the 100 pedigree replicates, the size of the final population varied between 67,467 and 136,613 individuals; the average size was 101,475, which corresponds well to the current size of the isolate.

In each simulation, a sample of 100 affected and 100 control individuals was picked by a slightly nontrivial procedure. Since we wanted to fix the disease model to a relatively common disease with a dominant model and high phenocopy rate in respect to any single disease-predisposing locus, we decided to set the mutation prevalence to 6/1,000. Thus, in each simulation, the aim was to have ~600 affected mutation carriers in the final population. To compute the mutation source and locus in a computationally effective way, we first selected 30 random points in the 100-cM chromosomal region that were considered as possible mutation loci. This selection was repeated in each iteration. After the chromosomal segment data were generated, the resulting prevalence for each possible combination of a founder chromosome and a mutation locus was computed. We then picked a combination that produced the desired overall mutation prevalence of 6/1,000 in the final population as accurately as possible. Since there were 198 unrelated founder individuals and 30 possible mutation loci, a total of 11,880 possible source/locus pairs were considered in each iteration, which turned out to be more than enough to produce the desired mutation prevalence accurately. Out of the ~600 resulting affected carriers, we then picked random samples of 20, 15, 10, and 5 individuals to produce mutated chromosome frequencies of A=~10%, ~7.5%, ~5%, and ~2.5%. The rest of the affected sample was chosen from non-carrier individuals to produce the phenocopies. No siblings were allowed to appear in the samples.

It is well known that in case-control studies, closer kinship in the affected sample may cause false positive results because of extra background linkage disequilibrium everywhere in the genome. To overcome this problem, we used family-based pseudo-control chromosomes. This was done in practice by taking the alleles in the non-transmitted chromosomal segments of the parents of each affected individual and labeling them as control chromosomes. In each simulation, a total sample of 400 chromosomes was taken, of which 200 were affected and 200 control.

We treated the haplotypes obtained from the simulator as given, which corresponds to error-free haplotyping. However, this is not in any way a prerequisite for applicability of the method according to the invention, as is demonstrated in experiments with missing and erroneous data. The entire sampling procedure corresponds to a standard case-control study setup with a pseudo-control sampling approach, where a dominant disease with high prevalence (0.03–0.12) is observed, and the phenocopy rate is high, but unknown at the time.

To accommodate the fact that ever-increasing informativeness of marker maps may soon facilitate whole-genome LD mapping, we used relatively dense and informative marker maps with intermarker intervals of exactly one cM. Since the usefulness of a marker depends solely on its informativeness, we did not want to fix number of alleles in each marker but instead fixed the informativeness of every marker to 0.7, as measured by the polymorphism information content (PIC). Typically, each generated marker contained 4–8 alleles, whose frequencies were less equally distributed as the number of alleles increased. The markers were created using a brute-force algorithm, where large numbers of markers with variable allele frequencies were produced, but only the small minority with desired PIC was approve.

Example 2

Parameters

We performed extensive gene localization experiments with different parameter values. For a basic setting, within which we compared the performance of the method in different data sets, we selected the following parameter values. The maximum length of haplotype patterns was restricted to seven consecutive markers, which corresponds to segments of 6–8 cM. This is close to the average length of shared haplotypes in a population of about 500 years of age. To allow for reasonable flexibility, at most two gaps were allowed per haplotype, and their lengths were limited to one marker. These parameter values prune patterns which are not biologically conceivable (unreasonably long haplotype patterns, or those consisting mainly of gaps) and, from a practical point of view, they allow faster execution and experimenting with the method than more flexible parameters. With these parameter values, localization time for one simulated data set on a 400-MHz Pentium PC was around one minute. The association threshold for the signed $\pm\chi^2$ measure was set to $\chi=9$, on the basis of our earlier work on similar data and methods and some experimenting. To ensure that the selection of these particular values is not critical for the method and to assess the robustness of HPM in this respect, we also experimented using patterns with unlimited length, with longer gaps, and without gaps.

Example 3

Localization Accuracy

Figure 1C:
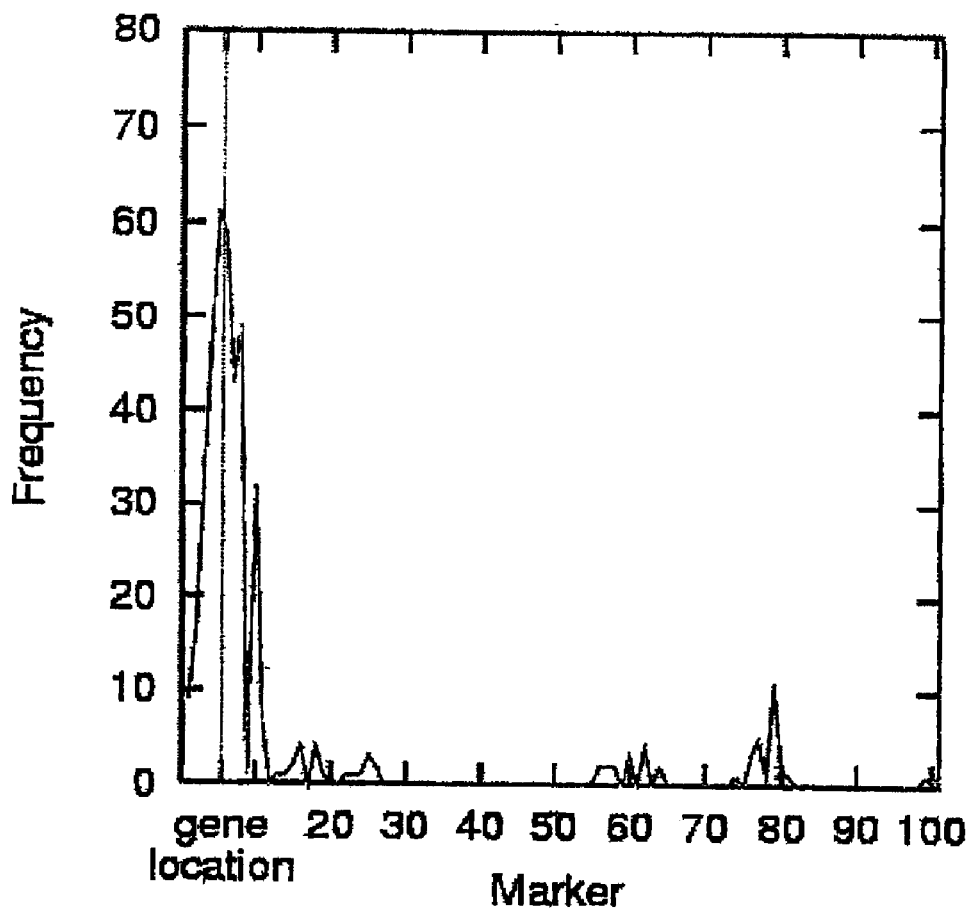

To illustrate the HPM method, FIG. 1A shows the list of 11 most strongly disease-associated haplotype patterns in a simulated data set with A=10% (10% of disease-associated chromosomes carry the mutation; no missing or corrupted data). The chromosome has 101 markers, but the patterns with strongest association occur between markers 1 and 6. The bottom line gives the marker frequencies for these markers, and the frequencies are also plotted as a histogram in FIG. 1B. Markers 2–4 have the highest frequency, closely followed by markers 5 and 1. The true gene location is in this data set halfway between markers 5 and 6 (depicted by a dashed vertical line). FIG. 1C shows a frequency histogram for the same data set, but this time with all haplotype patterns exceeding the association threshold of 9. Marker 5 has now the highest frequency and is therefore predicted as the gene location; a vertical line shows, again, the true location at position 5.5.

Figure 1D:
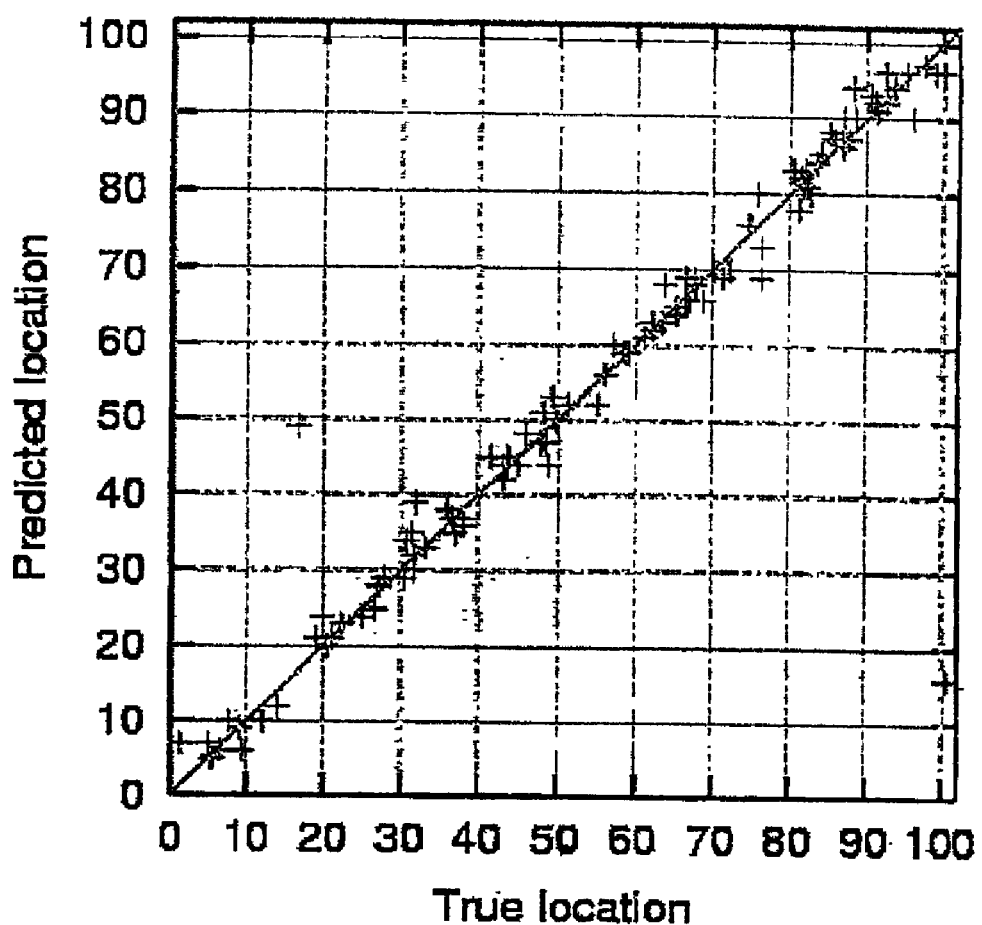

The true versus predicted locations for 100 simulated data sets with A=10% are shown in FIG. 1D; the data set of FIG. 1C is represented by a cross at (5.5, 5).

Figure 2A:
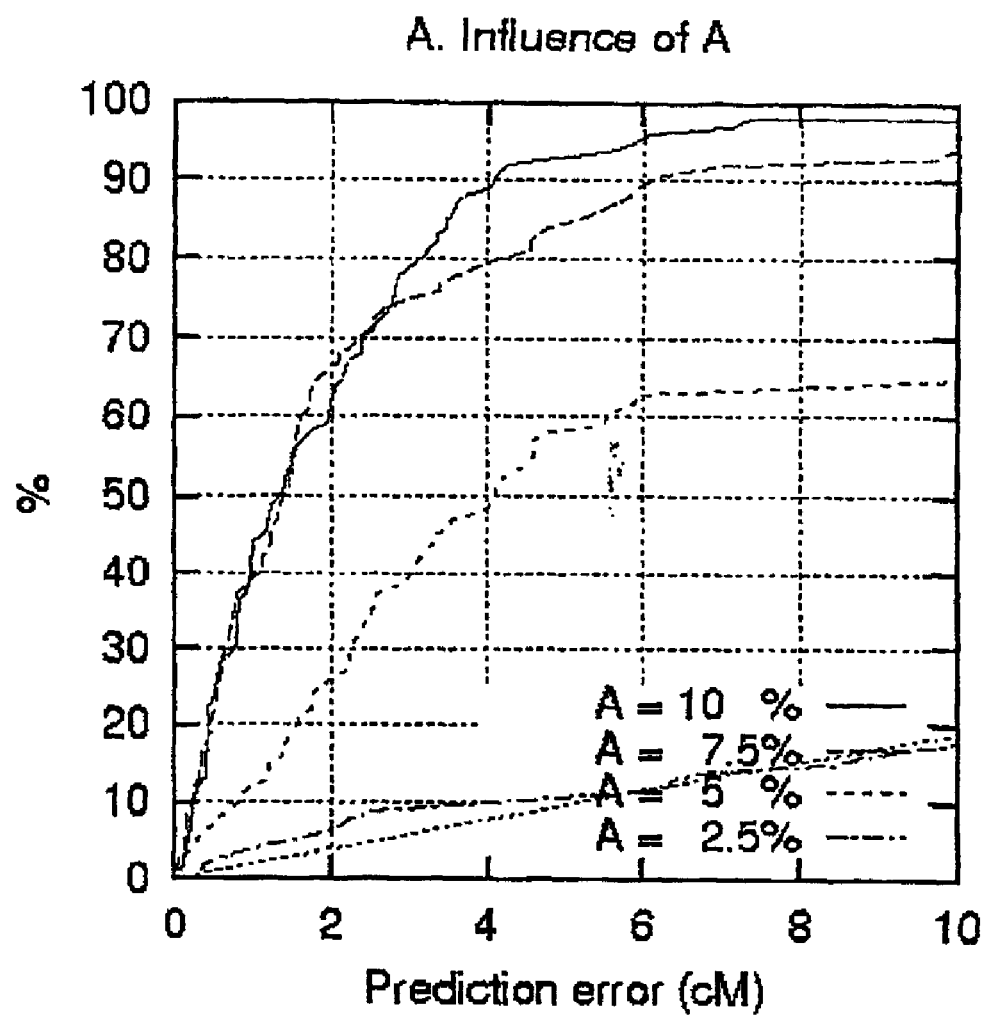
FIG. 2. The effect of various factors on prediction accuracy. The y axis shows which fraction of simulated data sets is within the error bound given on the x axis (i.e., y=P[error x]). The lowest, dotted curve is the prediction accuracy of random, uniform guesses. A. Effect of A, the proportion of DS mutation carrying chromosomes. B. Effect of doubled sample size (400 disease-associated and 400 control chromosomes). C. Effect of corrupted data. D. Effect of missing data. E. Comparison of prediction methods. The three topmost curves have been obtained with 0% corrupted and 0% missing data; the lower curves with 1% corrupted and 20% missing data. F. Effect of pattern search parameters. "HPM baseline": haplotype pattern searching as before; "no gaps": haplotype pattern searching without gaps; "single": the middle point of single most strongly associated haplotype without gaps is used for predicting the localization; "long gaps": gaps of up to three markers allowed; "long haplotypes": no length limit on the pattern lengths.
Figure 2:
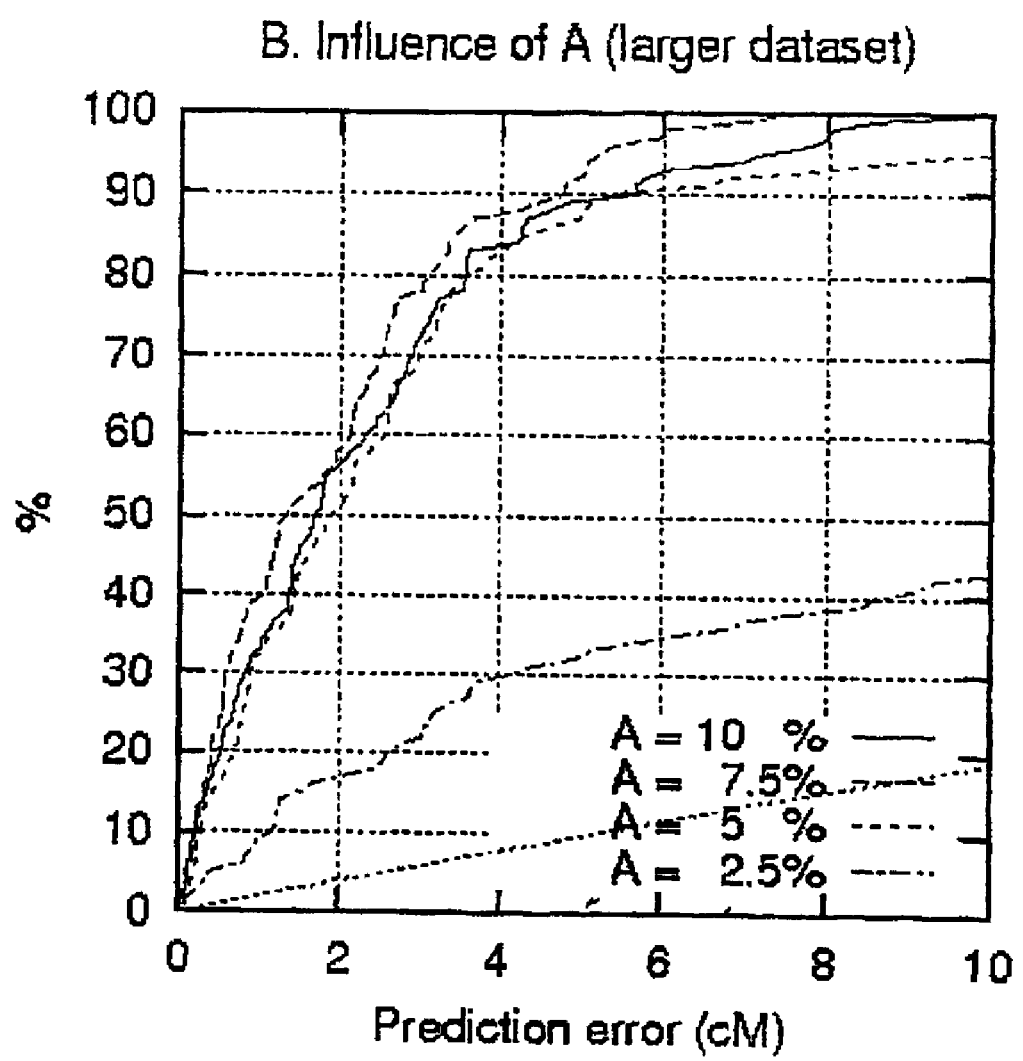

Overall, the predicted location shows good agreement with the true location. The localization accuracy and the effect of phenocopies was explored in more detail by plotting curves similar to power graphs: the height of the curve shows the fraction of data sets for which the localization was successful, as a function of the allowed localization error (FIG. 2A). The solid line represents the results given by FIG. 1d: for instance, in 90% of the simulations the error is 4 cM. For A=7.5% the accuracy is near that for A=10%, but for A=5% a clear drop can be observed and for A=2.5% the localization method does not perform significantly better than random guessing. Our explicit aim was to test realistic (small sample sizes) but difficult (2.5% A 10%) cases, in order to explore the limits of the method—which in this case and with respect to A seem to be somewhere around A=5%. For larger samples and lower phenocopy rates, the results should obviously be at least as good as those presented here.

The effect of sample size was examined by doubling the number of both chromosomes—that is, with data sets of 400+400 chromosomes (FIG. 2B). Compared to the smaller data set (FIG. 2A), the localization accuracy improves significantly for low values of A (A=5%, 2.5%); for larger values of A, there is not much difference. It is a coincidence that localization accuracy seems slightly better for A=7.5% than for A=10% in FIG. 2B.

Figure 2C:
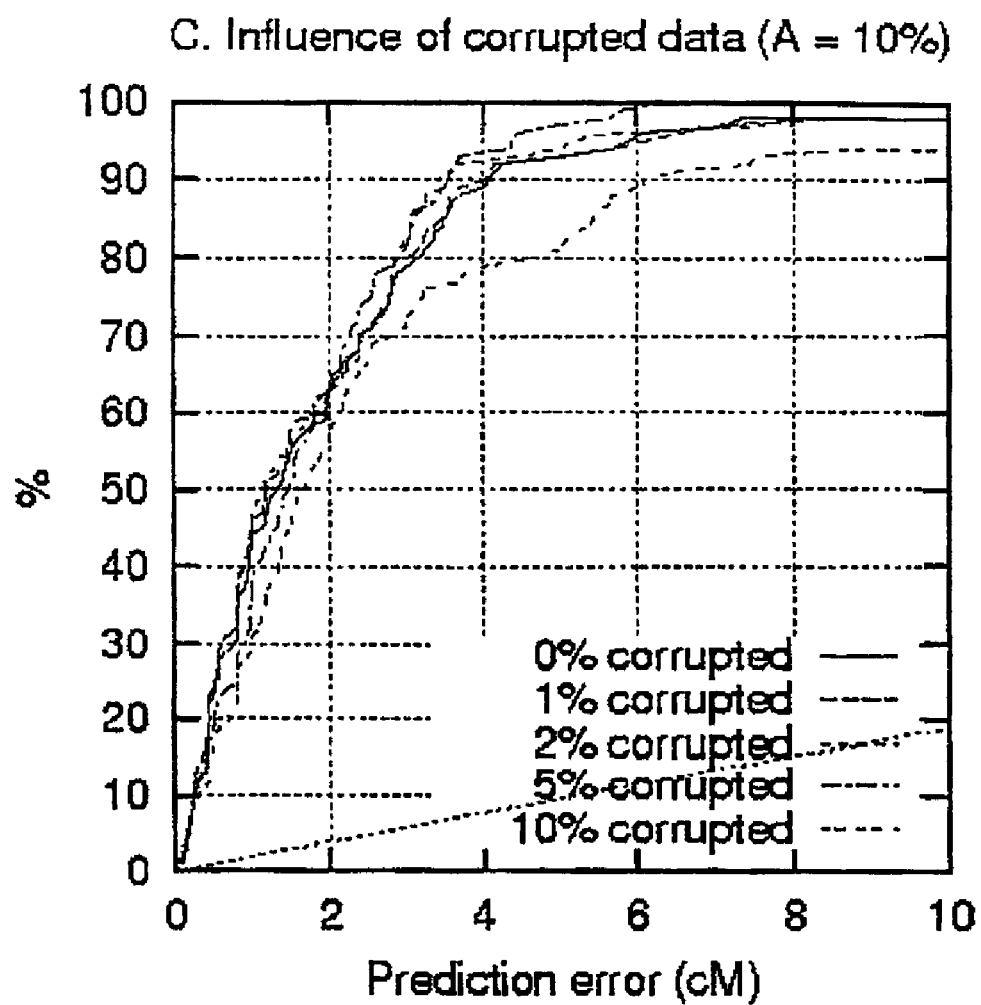
Figure 2D:
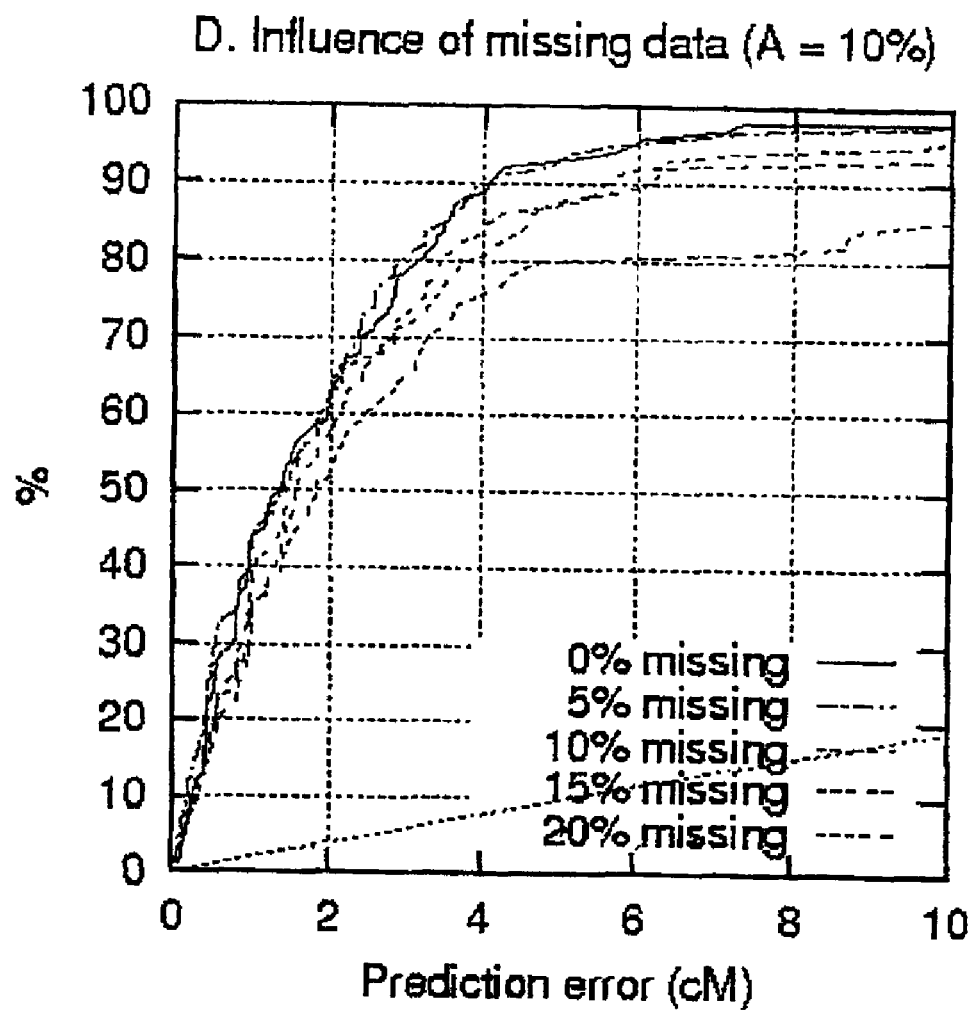

The effect of corrupted data, i.e., genotyping errors and sporadic marker mutations, was tested by randomly changing alleles in the data. FIG. 2C shows the influence of having 10% of data corrupted (with A=10%). Marker mutations were not modeled in simulations, but the mutation process— involving the coalescence of the mutated allele through generations to several persons with the common mutation in the final study population—should actually make the associations easier to detect than random changes of alleles do. The influence of having up to 20% missing data was explored in a similar manner (FIG. 2D, A=10%). The effect of missing data corresponds to that of corrupted data, as could be expected. There is hardly any difference in the accuracy with 0%–5% of data corrupted or missing. Higher proportion (10%) results in a slight decrease in performance. The combined effect of corrupted and missing data contained no surprising interactions.

Figure 2E:
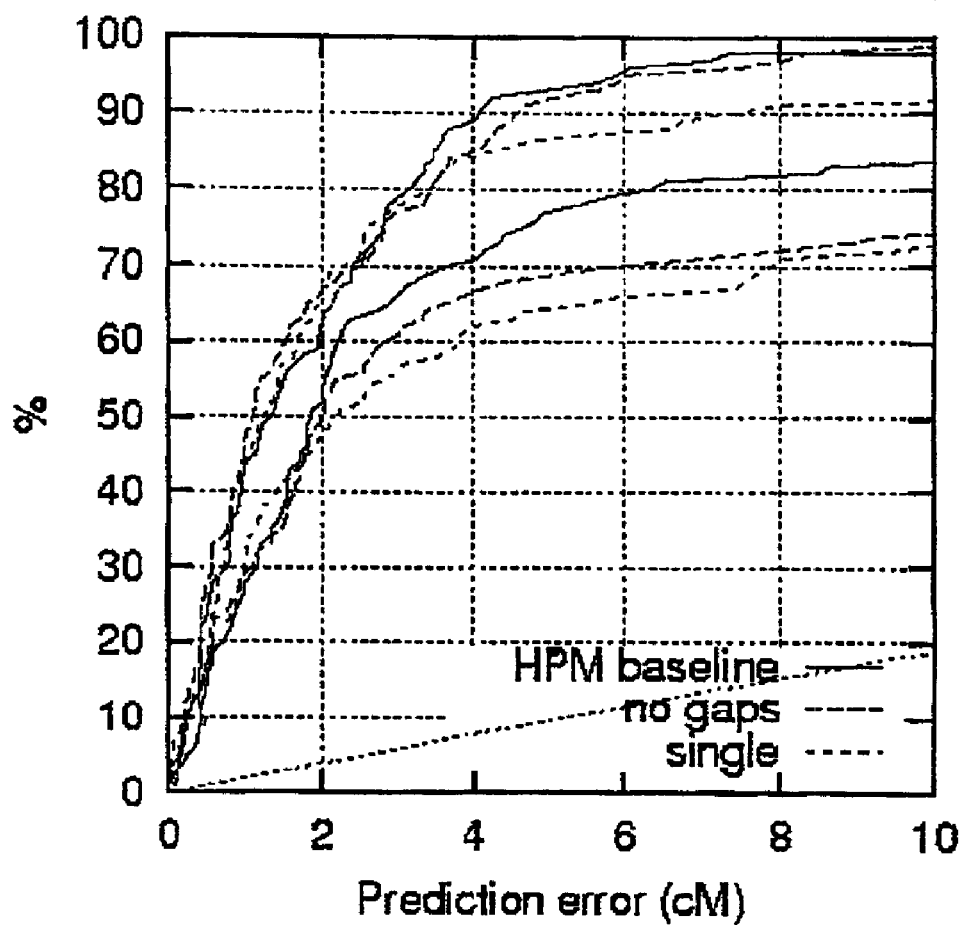
Figure 2F:
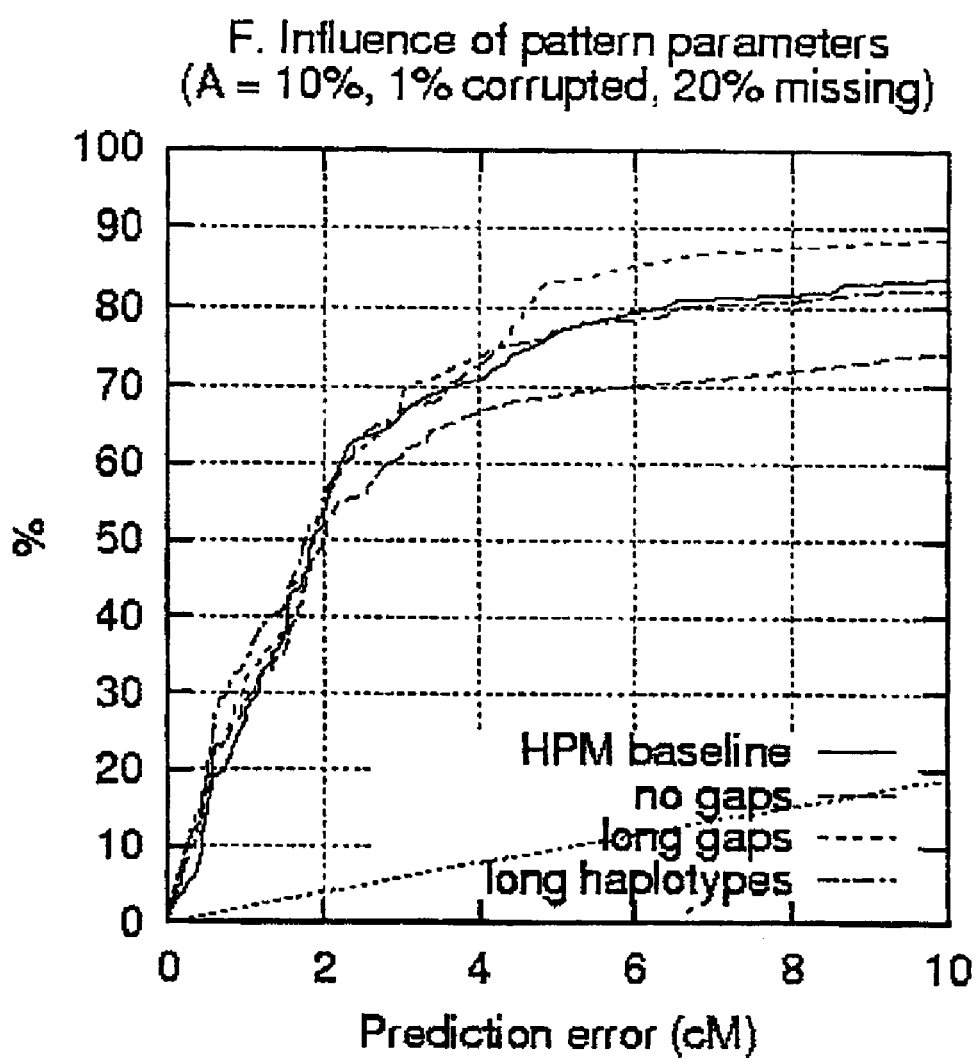

The HPM method was compared to two simpler alternatives (FIG. 2E, A=10%). The first one was to take the single most strongly associated haplotype without gaps and to predict the DS locus to be in the middle of that haplotype. The second was to localize with haplotype patterns without gaps. With correct data (three higher curves), there is not much difference between the performance of the methods for error bounds <4 cM. More differences appear as corrupted and missing data are introduced (lower three curves), and the HPM method seems to outperform the other methods by finding the approximately correct region more consistently. In order to assess the robustness of the method with respect to the selection of pattern search parameters, simulated data with A=10%, 1% corrupted and 20% missing, was re-analyzed (FIG. 2F). The effect of gaps in the patterns was evaluated by either prohibiting gaps (as in FIG. 2E) or by allowing the gaps to be up to three markers long instead of just one. In addition, a test was run where the length of the haplotype patterns was not limited. Differences start to appear at error bounds of at least 2–4 cM; allowing longer gaps improves the performance somewhat, whereas prohibiting gaps altogether results in a decreased performance.

Example 4

Localization Accuracy with Permutation Tests

Figure 3A:
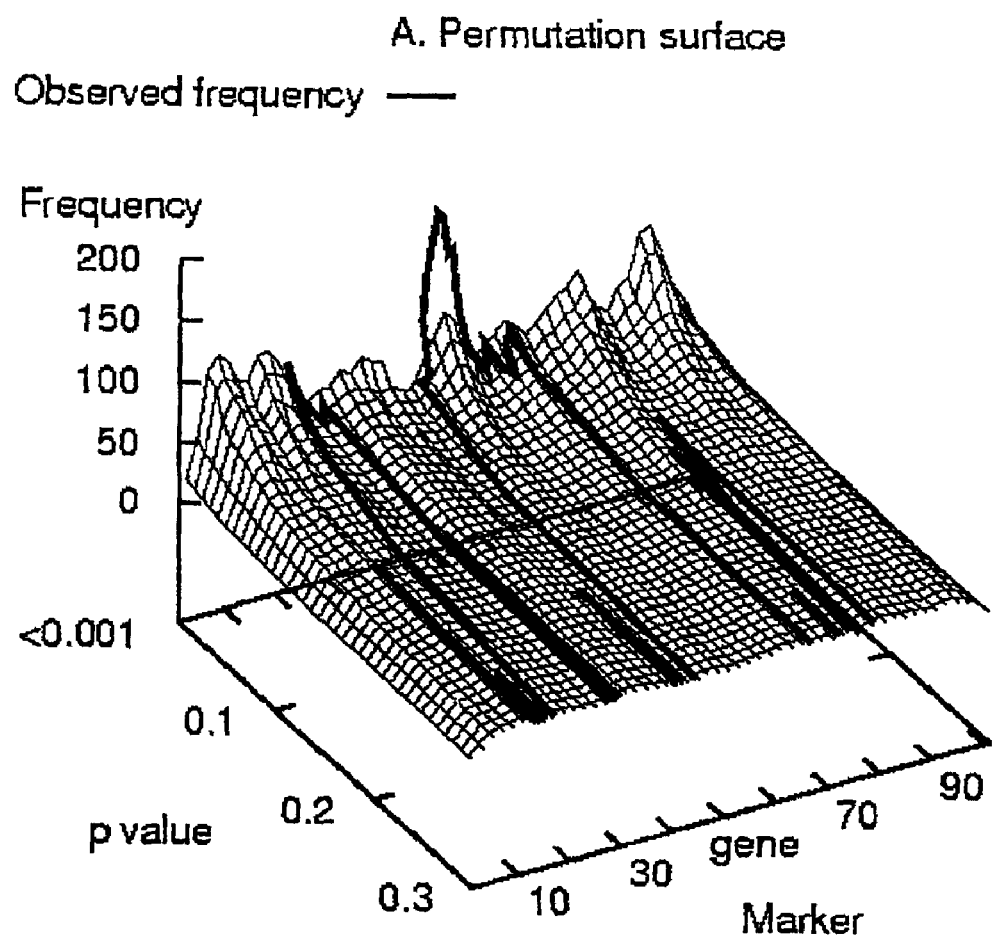
FIG. 3. Permutation tests with a simulated data set with A=7.5%. A. The permutation surface. The height of the surface at point $(i, p_i)$ is the marker frequency of marker $m_i$ that has an estimated marker-wise P value of $p_i$. The observed frequency is plotted on the surface by projecting it from the marker frequency plane onto the permutation surface. The closer the line gets to the 'back wall', the more significant is the marker frequency. B. Marker frequencies for different P values. The solid line shows the observed marker frequencies in the simulated data; the dashed lines have been plotted by connecting marker frequencies for which the marker-wise P values are the same. C. Marker frequencies for different P values in an unsuccessful localization. The solid line shows the observed marker frequencies in the simulated data; the dashed lines have been plotted by connecting marker frequencies for which the marker-wise P values are the same. D. The effect of permutation tests on the prediction accuracy, with 100 data sets where A=5%. The solid line represents localization accuracy without permutations, and the dashed lines show the prediction accuracy with the smallest marker-wise P value ("min p"), or with the smallest P value at most 0.01 or 0.001. If the smallest P value is >0.01 or 0.001, no prediction is made at all; the fraction on y axis is computed among the predictions made. The lowest, dotted curve is the prediction accuracy of random, uniform guesses.
Figure 3B:
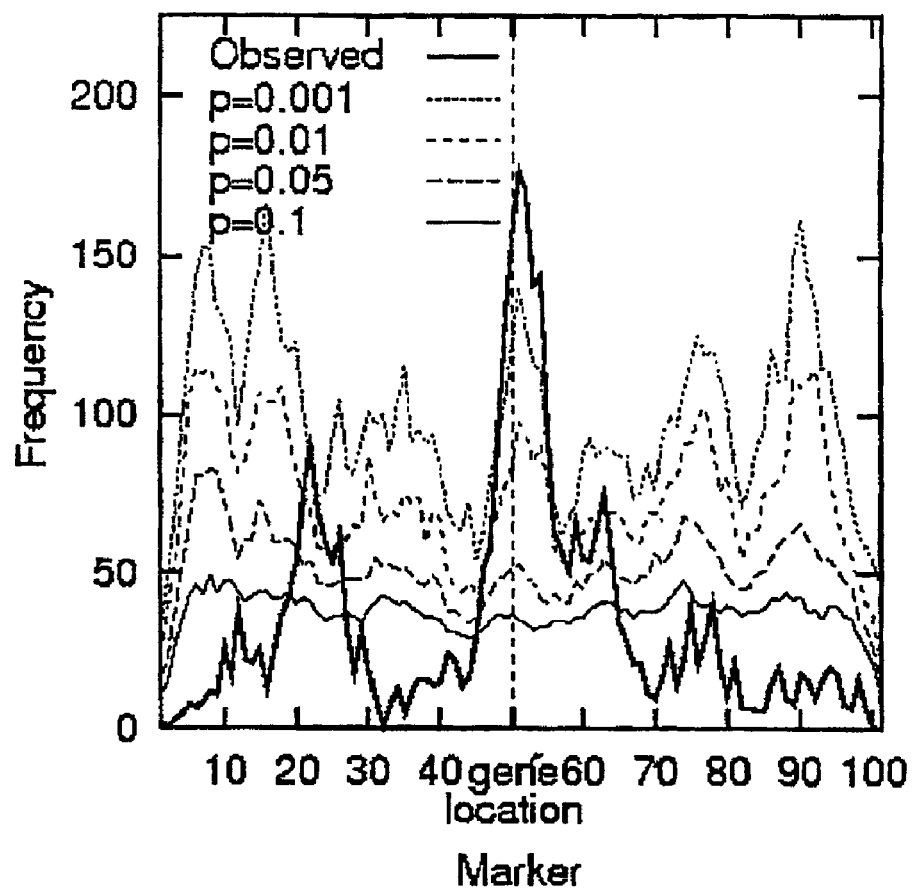
Figure 3C:
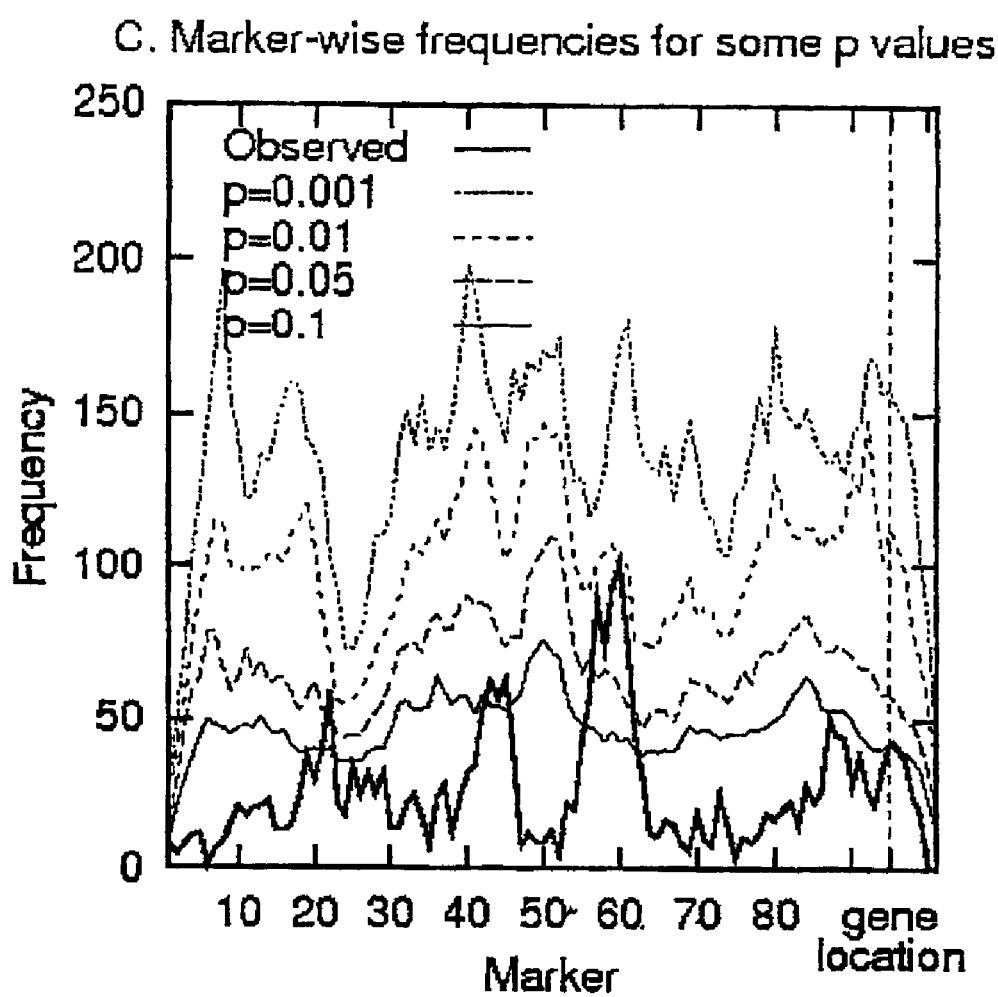

Permutation tests were used to obtain more information about the significance of observed marker frequencies. Markerwise P values were used to sort markers by their statistical unexpectedness, not to test the statistical significance of the findings. The experimental results obtained with 1,000 random permutations show that the peaks observed in marker frequencies in the vicinity of DS locus typically clearly surpass those produced by background LD. The permutation surface for a simulated data set with A=7.5% is shown in FIG. 3A; FIG. 3B gives similar information in two-dimensional form. The true DS gene location was at point 50.2, and the lowest P values, P<0.001, were obtained around it at markers 46–56. FIGS. 3a and 3b represent a typical successful case: the marker frequency is highest close to the DS locus, and permutation tests confirm this finding. An unsuccessful localization is in turn shown by FIG. 3C; the highest marker frequencies and the best markerwise P value, ~0.01, are obtained for marker 60, but the true DS locus is at position 95.0.

Figure 3D:
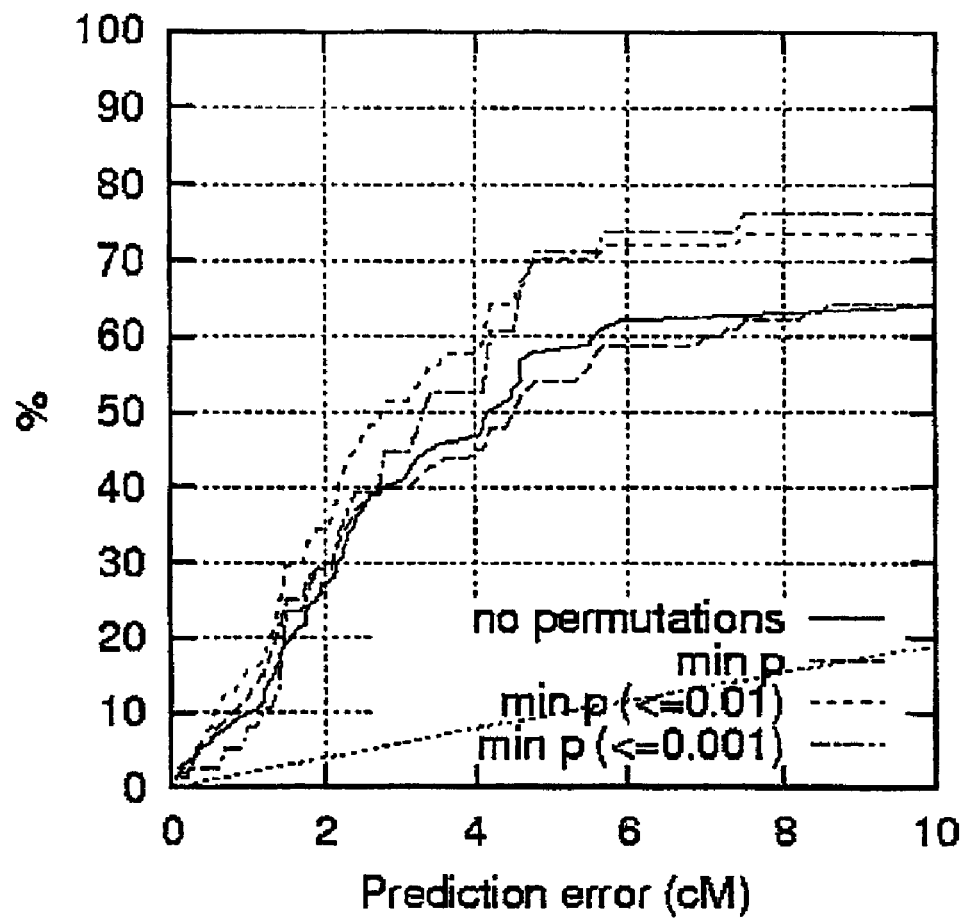

We performed the following experiments in order to see if the prediction accuracy can be improved by permutation tests. We predicted the location of the DS gene to be at the marker with the smallest P value instead of the most frequent marker. Optionally, given a threshold for the P value, we made a prediction only if the best P value was below the threshold (and otherwise replied "don't know"). The localization accuracy is somewhat improved by employing permutation tests (FIG. 3D, A=5%). The improvement was less evident with A=7.5%, and with A=10% this modification had practically no effect. For A=2.5%, again, there is no improvement with the sample size of 100 affected individuals.

Example 5

SNP Data

We performed experiments with artificial SNP data to test the utility of the HPM method with biallelic markers. An increased density of markers was used (3 SNPs per 1 cM) to maintain the overall information content roughly at the same level with the microsatellite markers. A higher density is also motivated by the willingness to increase the density of markers in an interesting region. Additionally, it is expected that genomewide scans at higher densities of SNPs will be possible in the near future. Missing information was simulated by randomly removing 12.5% of the alleles. This was done in order to mimic the effect of haplotyping ambiguities with SNP markers, expected to occur whenever a family trio, both parents and the only offspring, are heterozygous in a given locus. The pattern search parameters were modified slightly, to account for the higher density of markers; the maximum length of a haplotype pattern was 21 markers (~7 cM). The maximum number of gaps was two, and the maximum length of a gap was one marker.

Figure 4:
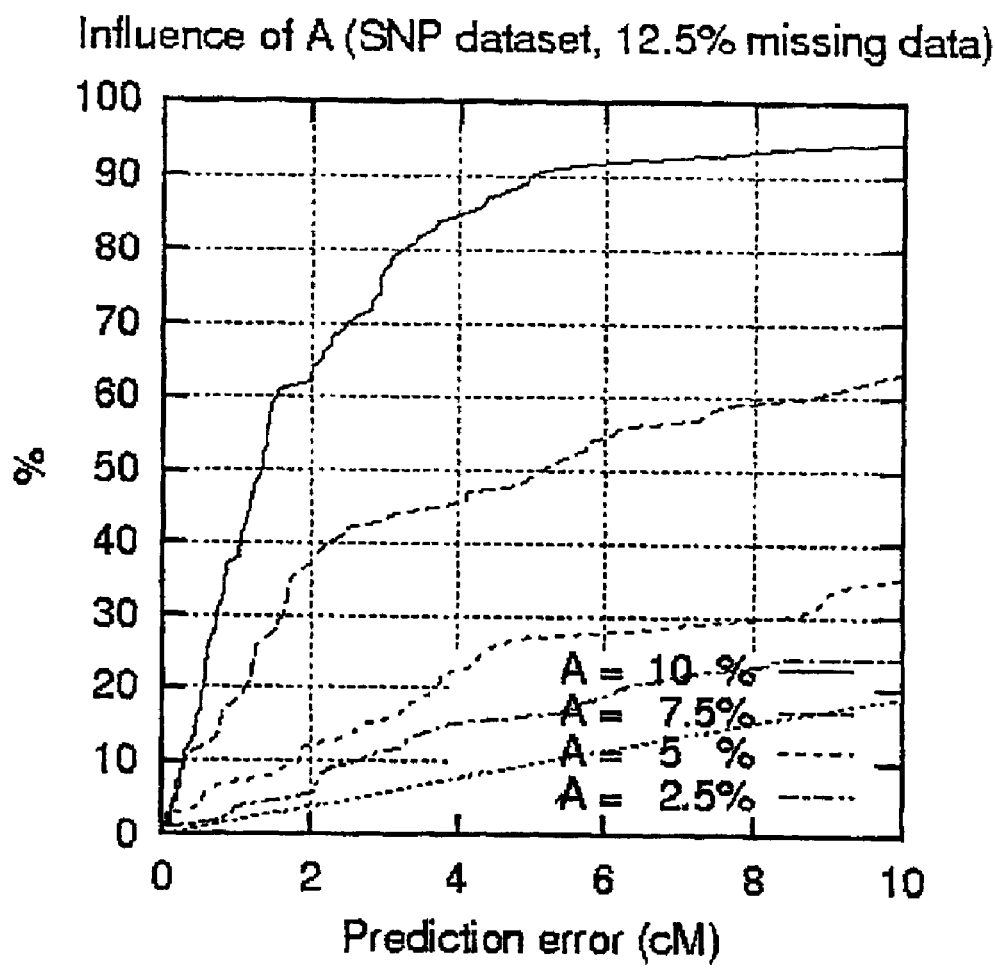
FIG. 4. Effect of A, Proportion of DS mutation-carrying chromosomes, in the single-nucleotide polymorphism (SNP) data.

The results (FIG. 4) show that the HPM method performs well with the simulated biallelic data. For A=10%, the accuracy is close to that of complete microsatellite data (FIG. 2a), despite the 12.5% of missing data; with smaller values of A the accuracy drops somewhat faster than with complete microsatellite data. Overall, the localization accuracy with 3 SNPs per 1 cM in these data sets is close to that of a map with 1 microsatellite per 1 cM.

Example 6

Real HLA Data

We applied our method to a real data set, consisting of affected sib-pair families with type 1 diabetes from the United Kingdom (Bain et al. 1990) that were genotyped for 25 polymorphic microsatellite markers. These markers covered a 14-Mb region including the entire HLA complex. The HLA-DQB1 and DRB1 loci, located in the center of these 14 Mb, are known to be the primary constituents of the major type 1 diabetes—susceptibility locus mapped to this region, designated as IDDM1. This data set was originally generated to apply the currently available tools of association fine mapping, in order to investigate the accuracy this locus could be mapped with. Using the multiallelic association test $T_{sp}$, it has been demonstrated that the HLA-DQB1 and DRB1 loci could be mapped with surprising accuracy, despite the tremendous strength of LD in that area.

To test HPM in a setting similar in sample size to the simulated cases, only 200 of the original 385 affected sib-pair families were used, and one of the affected offspring was selected randomly in each family. The control chromosomes were generated by including only the non-transmitted alleles or haplotypes. HPM was applied to this data set using the same parameters as described for the analysis of the simulated microsatellite data.

Figure 5A:
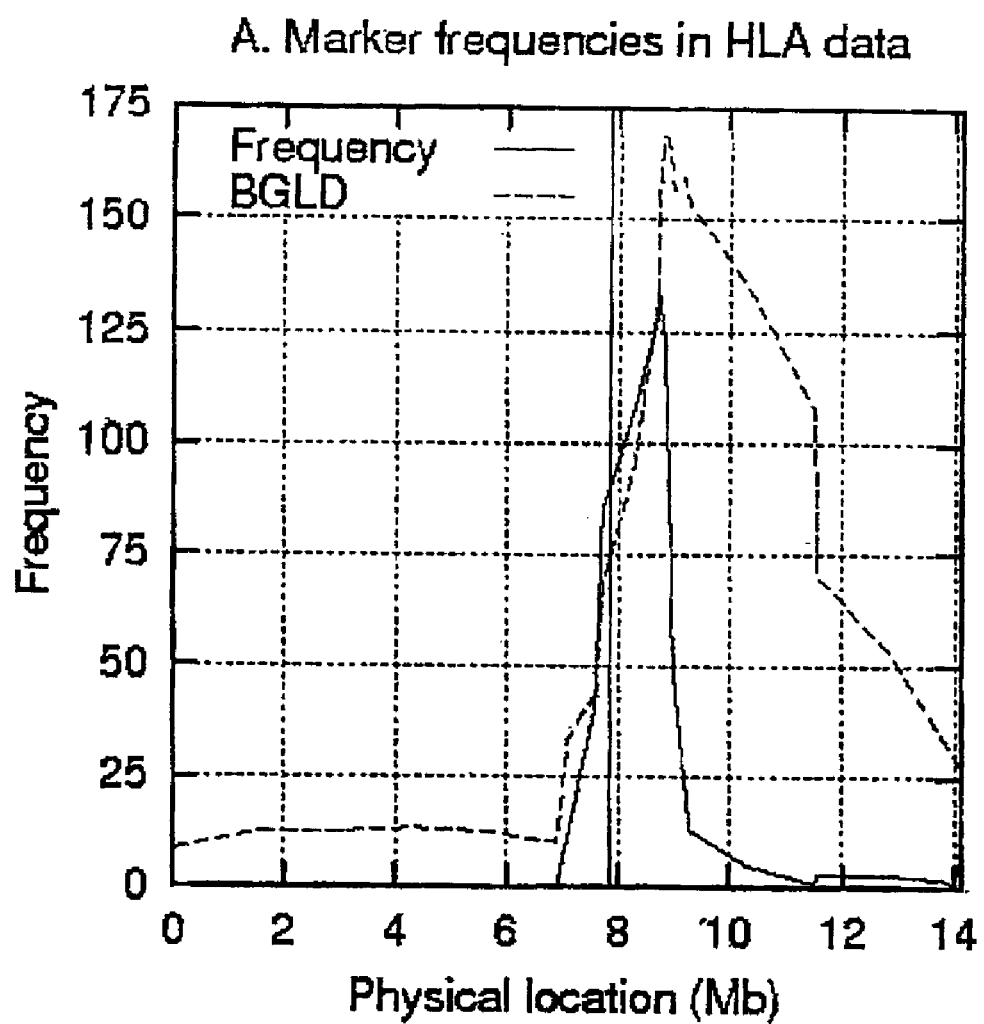
FIG. 5. Results on the real HLA data. A. Marker frequencies and background LD (BGLD), as measured by the marker-wise mean of the 10 highest frequencies obtained by 10,000 permutations. B. Negative logarithm of the marker-wise P values. The vertical line shows the gene location. The flat interval of -log p 9.21 is the upper limit of the score, due to the limited number of permutations. The ratio of the marker frequency to BGLD (dashed curve) was used for estimating the gene location inside this interval.
Figure 5B:
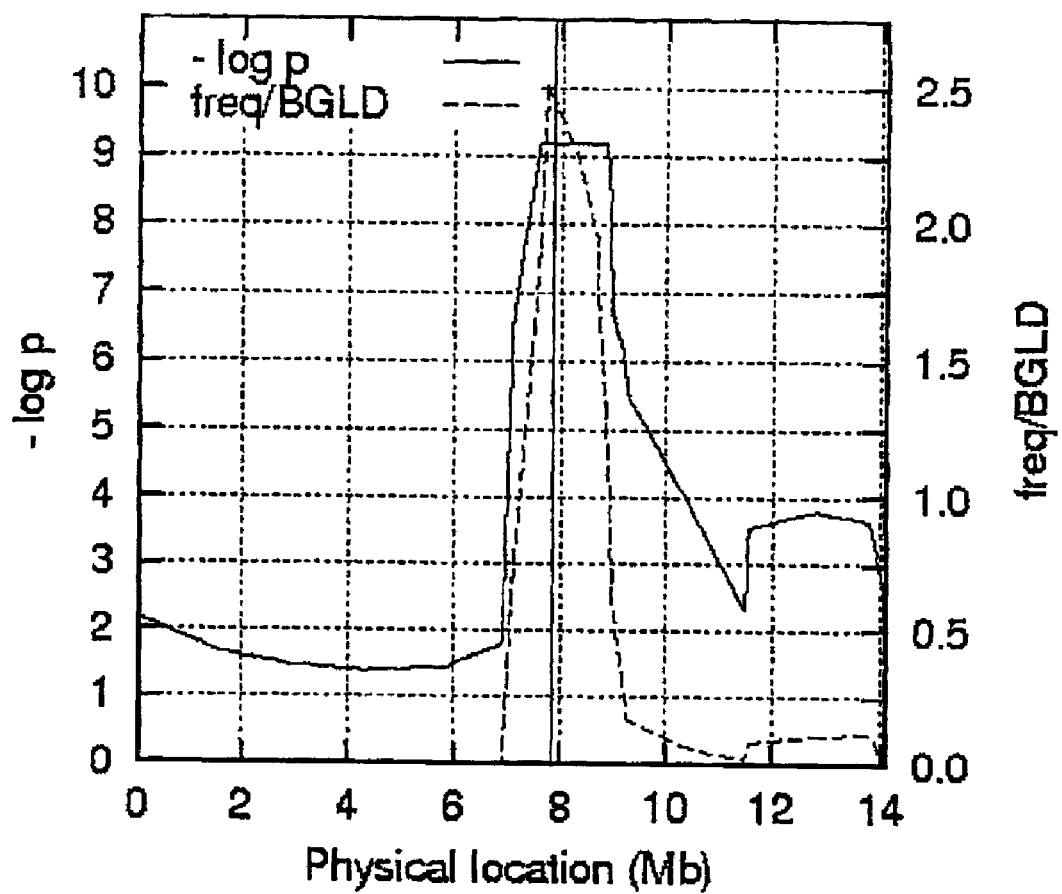

The results (FIG. 5) demonstrate that the method was capable of mapping the disease locus to the marker located closest to HLA-DQB1 and DRB1, that is marker D6S2444, even though background LD in the HLA and the telomeric end of the map was very strong. A comparison to the results of the $T_{sp}$ analysis shows that the mapping accuracy was similar with both approaches even though we used less information with HPM.

Example 7

Localization Accuracy for Two-Gene Diseases with Strong Allelic Heterogeneity Mapping of oligogenic diseases is an interesting problem for which the HPM method can be generalized. We performed preliminary experiments on simulated data sets that contained two DS loci in different chromosomes. Both DS loci included several disease mutations, each originating from a different ancestral haplotype (max. 5 ancestral mutations per locus). The effect of all disease mutations to the disease susceptibility was, for simplicity, the same. The combined frequency of mutation alleles in current population was 0.05 for both loci. The overall frequency of carriers of at least one mutation allele in each disease locus (i.e. A-B-) was approximately 9.5/1,000 individuals. The penetrances were defined to be 0.9 for individuals with at least one DS mutation in both chromosomes (A-B-), and 0.0001 for individuals with the remaining genotypes. The samples consisted of 100 affected and 100 randomly selected control individuals. Average genotype frequencies are summarized in Table 1. Table 2 shows the frequencies of the most frequent genotype in each genotype class, when different mutation alleles are not lumped together. For instance, the mean frequency of 0.7 for genotype class AaBB in the affected sample indicates that in average 0.7 affected individuals were heterozygous with respect to the same founder mutation in the first DS gene and, in addition, carry the same pair of founder mutations in the second DS gene.

Figure 6A:
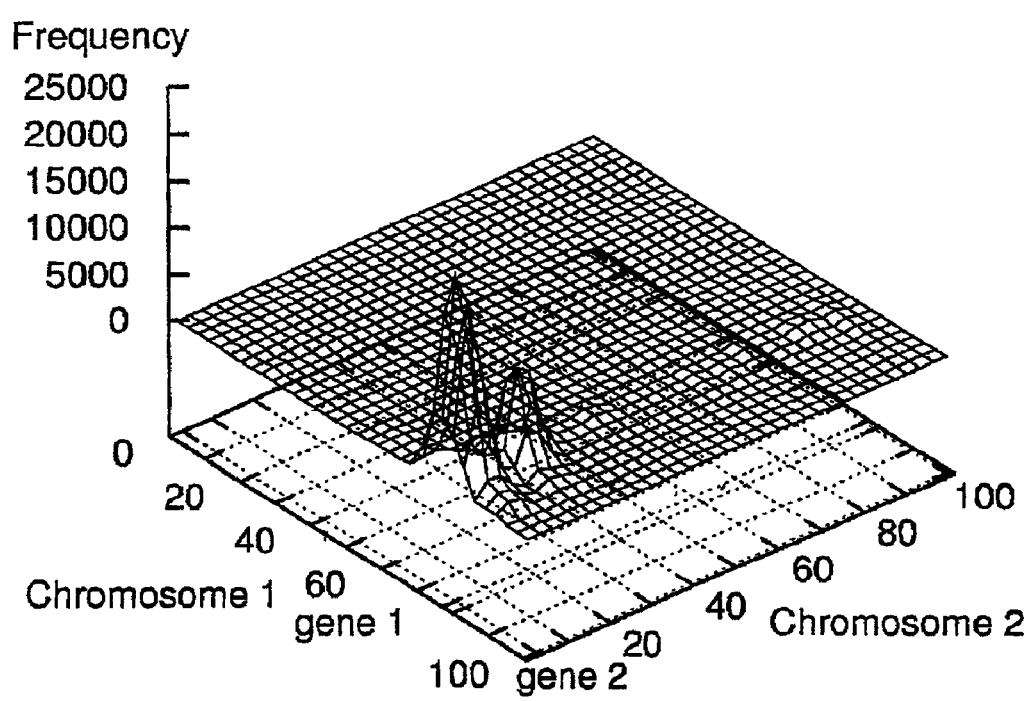
FIG. 6. A. Frequency histogram for pairs of markers from two chromosomes in three-dimensional from. B. The same in contour representation (contour line interval is 2,500). The true locations of the genes are 77.1 on chromosome 1 and 3.0 on chromosome 2. C. Prediction accuracy achieved in two-gene experiments; vectors represent the (Euclidean) residuals from the true locations (centers of the circles). D. The cumulative proportion of analyses (in 100 data sets) with residuals below the bound given by x axis. The dotted curve on the bottom is the prediction accuracy of random, uniform guesses for two gene locations.
Figure 6B:
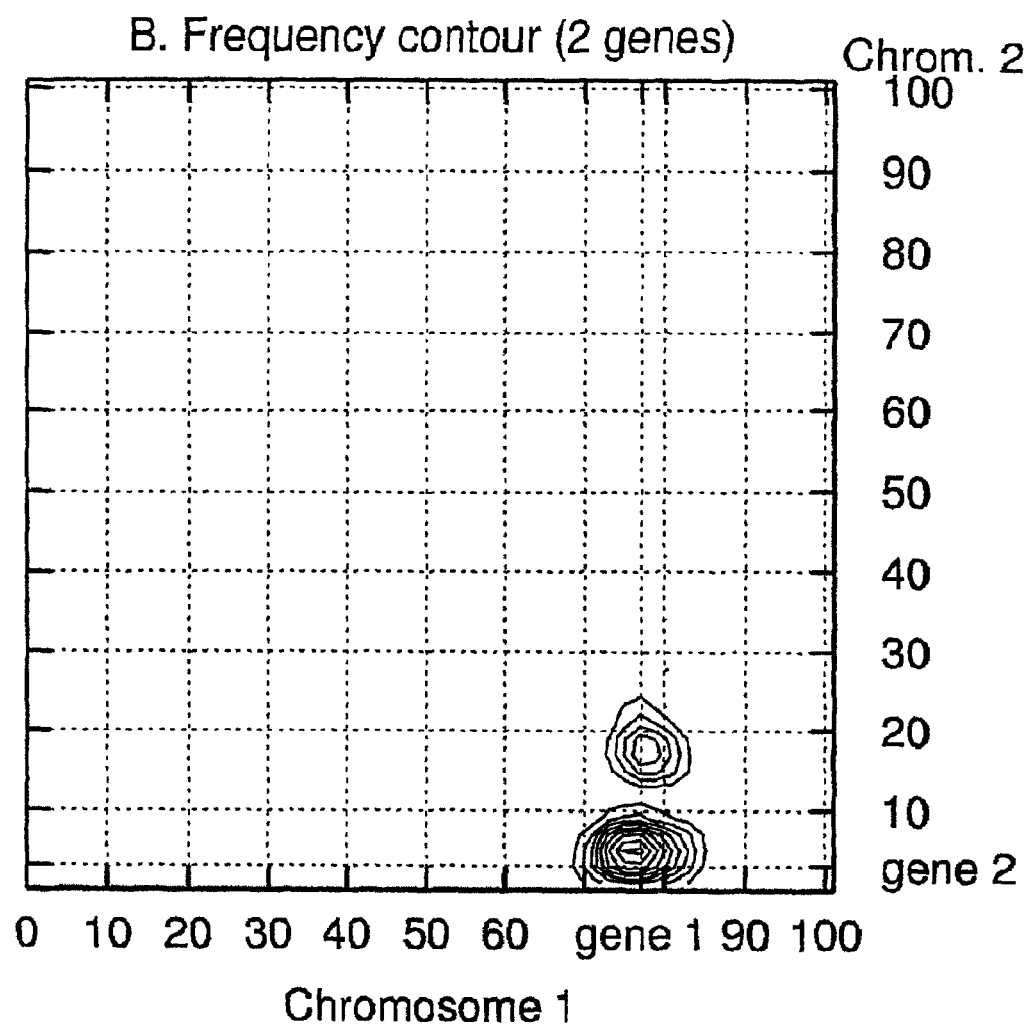
Figure 6C:
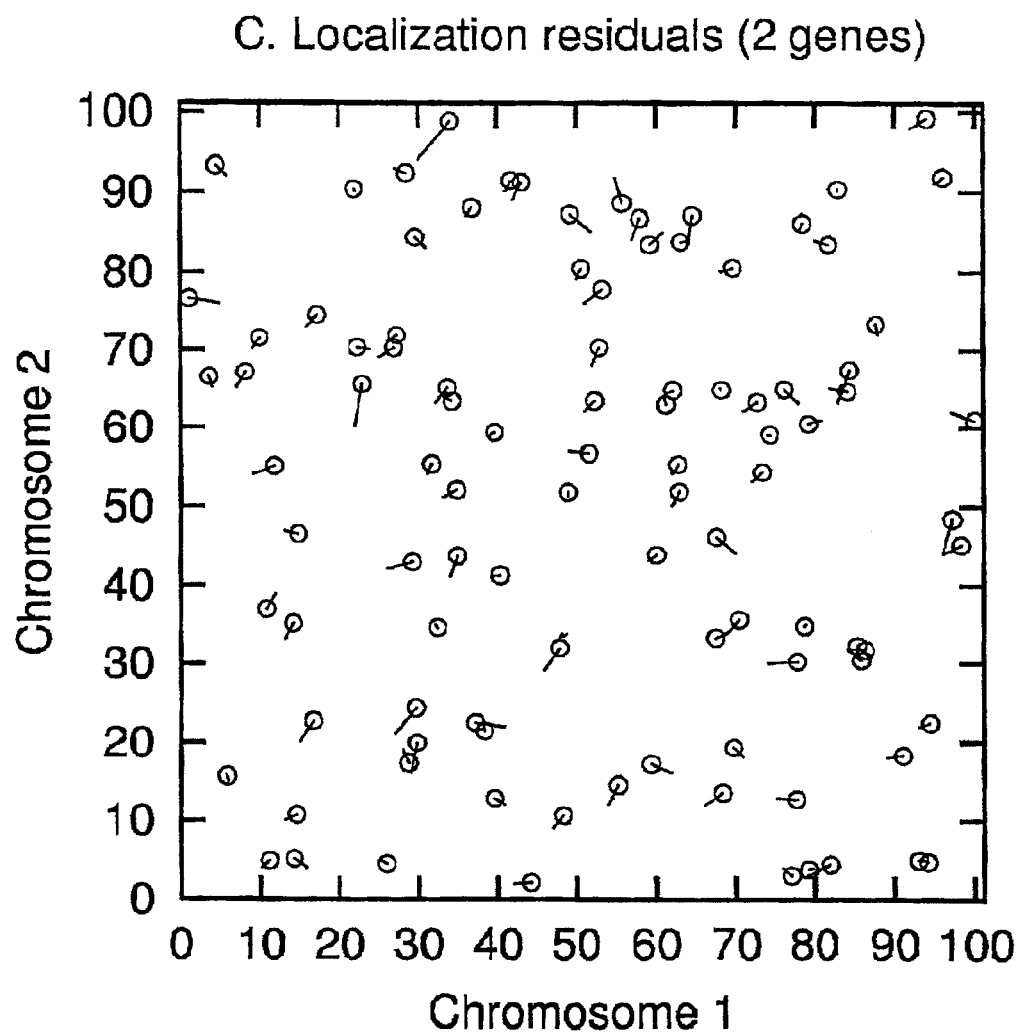
Figure 6D:
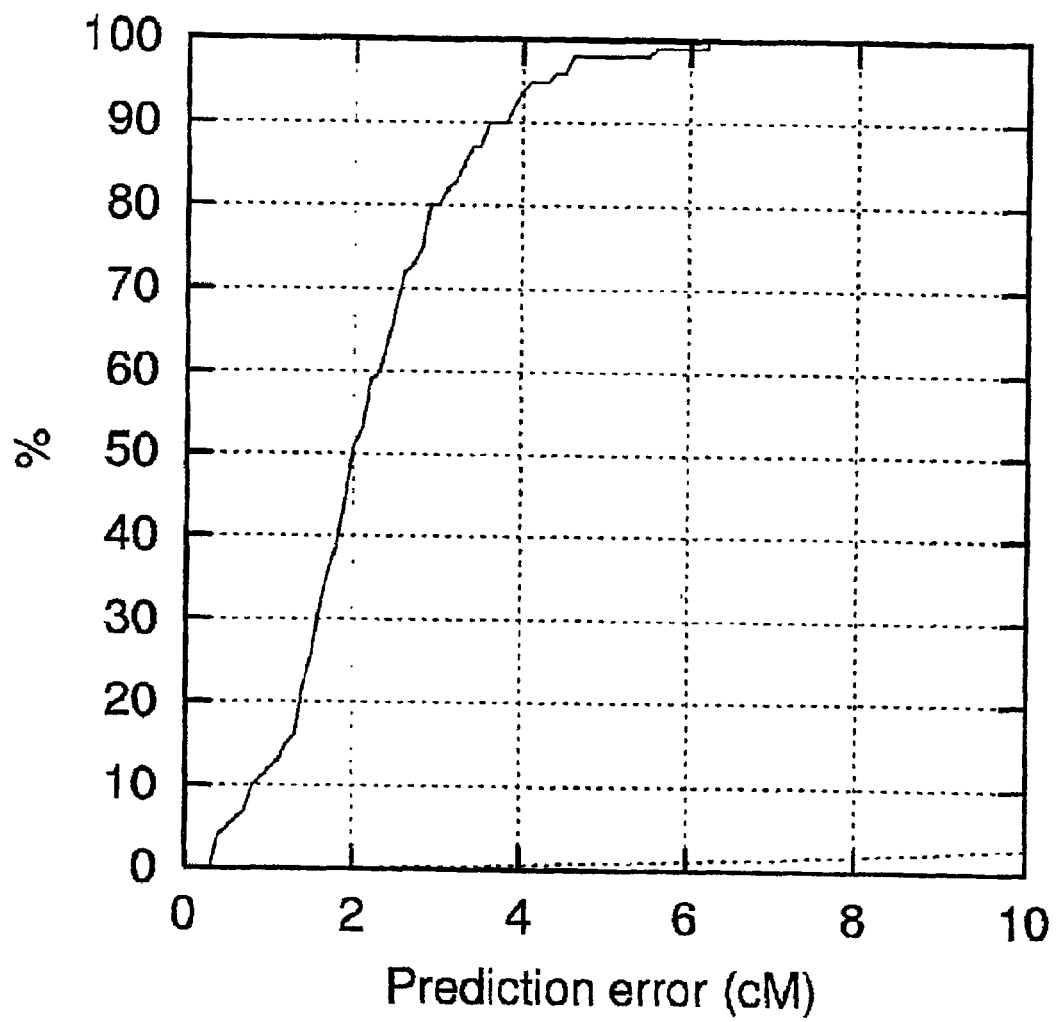

We carried out the two-gene experiments as follows. First, all the frequent haplotype patterns in the two chromosomes C1 and C2 were searched with the basic HPM algorithm, without considering the strength of their disease association. Then, new 'two-gene' patterns were formed by taking all pair-wise combinations between patterns on C1 and on C2. We evaluated the association measure for these patterns, and predicted the DS locations for both chromosomes simultaneously based on the marker scoring method and the two-gene patterns. It turned out that marker frequency surfaces generated by the strong two-gene haplotype patterns in the current datasets tended to have one strong peak, always in the immediate neighborhood of the DS gene (see FIG. 6 for an example). Experimental results with 100 data sets indicate that the localization accuracy is consistently high: FIG. 6C shows the 2-dimensional residuals, FIG. 6D gives the corresponding curve for prediction accuracy (in terms of the length of the residual vector).

Example 8

Genomewide Analyses

We carried out experiments on simulated data sets consisting of 250 affected individuals and their offspring. The simulated population had undergone exponential growth from 100 unrelated founder individuals to a current population size of 750,000 in the period of 40 generations. The inheritance of 100 cM founder chromosome pairs was simulated using Populus chromosome simulator, which resulted in the list of ancestral chromosome segments of each individuals in the last two generations.

The liability of each individual in the last generation was then computed from formula $L=x+2R$, where x is an indicator variable for the presence of one or more of disease-causing mutations, and R is a random number between zero and unity, corresponding to non-genetic effects. While the liability of each individual was computed, we set the threshold for being affected to such a value that a total of 2 percent of the final population became affected. Four disease-causing mutations were selected, each originating from one founder chromosome. The mutation sources were selected in such a way that, primarily, their total frequency among the last two generations was as close to 80,000 as possible, and, secondarily, the frequencies of the mutations were as close to each other as possible.

Next, random samples, each containing 250 affected individuals and their parents, were created. A map of markers spaced at intervals of 1 cM, each containing five alleles with frequencies of 0.3, 0.175, 0.175, 0.175, and 0.175, was then combined with the segment data, which resulted in artificial sets of allele data. Finally, the quantitative trait Q of each individual was computed from function $Q=2.5z+3S$, where z is an indicator variable for the presence of either of two (out of four) pre-specified mutations that are defined to cause an increase in the value of the quantitative trait, and S is a random number between zero and unity.

Finally, the haplotypes were deducted using the genotype data of individuals and their parents. Hence, the outcome of the simulation procedure consisted of data sets of 250 affected individuals as well as values of quantitative trait Q.

Figure 7A:
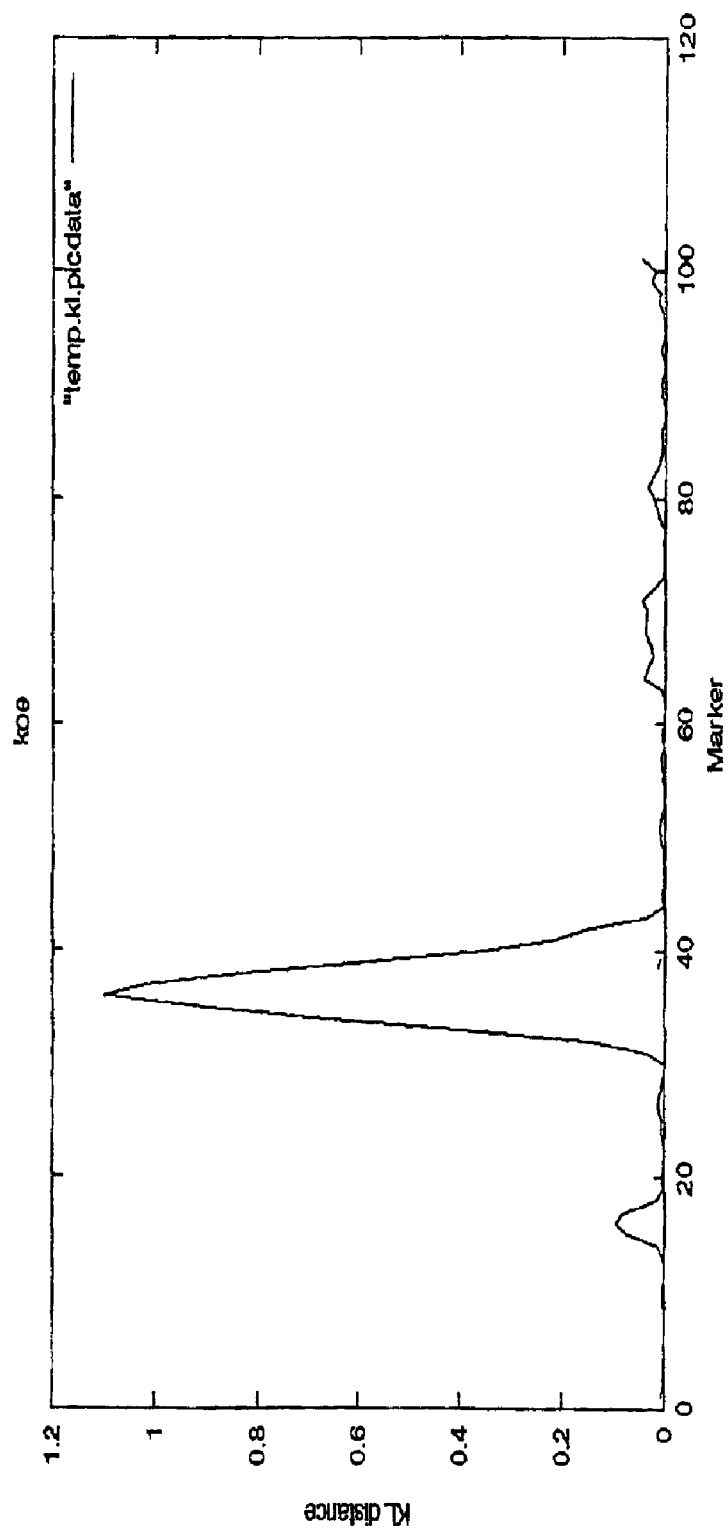
FIG. 7. A., B. Results for experiments on simulated data sets consisting of 250 affected individuals and their offspring.
Figure 7B:
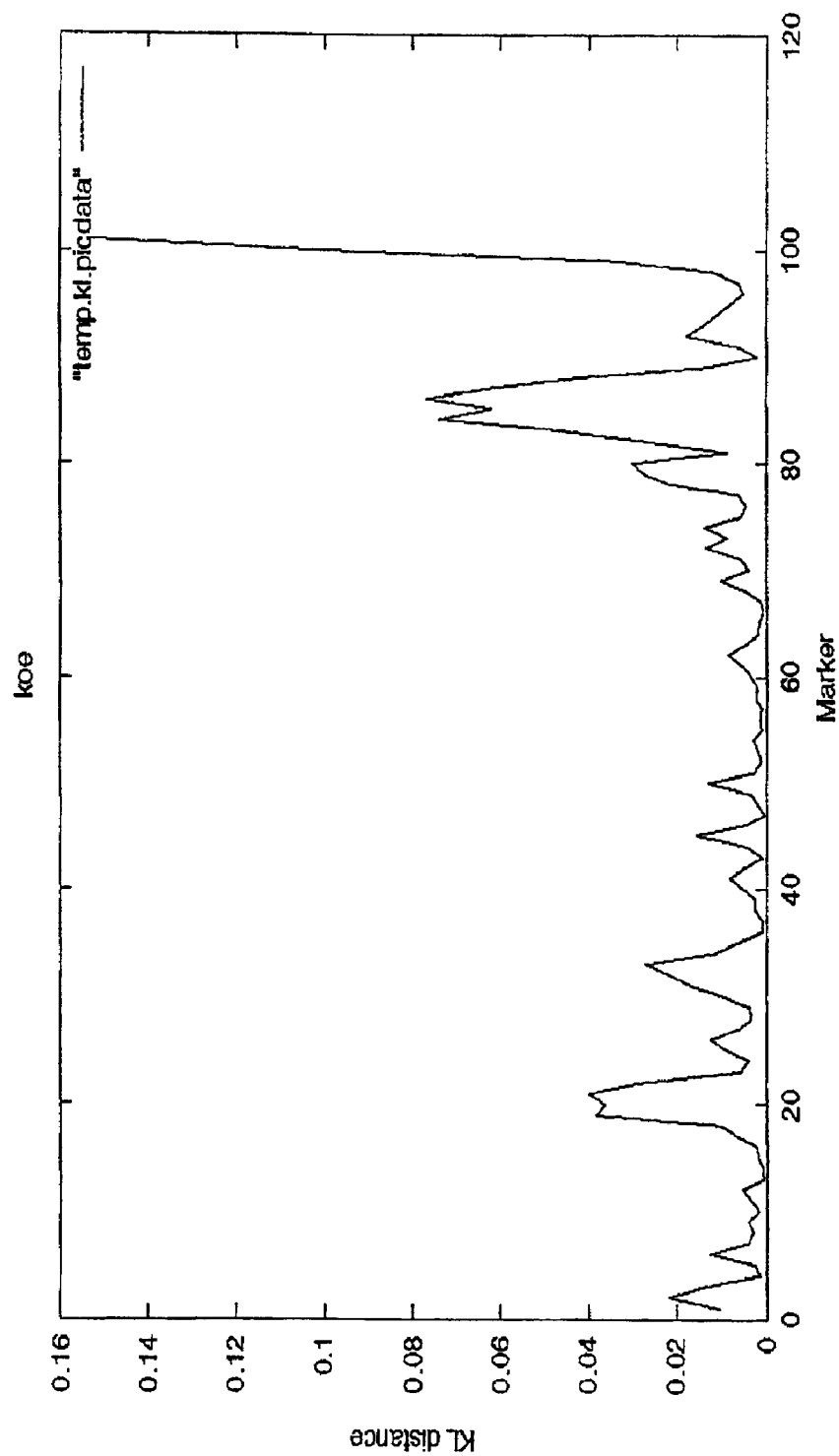

Two examples of correct localizations are shown in FIG. 7. The correct locations of the genes are markers 37.25, and 100.76, respectively.

Example 9

Candidate Gene Analyses

The method according to the invention was used to analyse SNP data from candidate genes GENE1 (chr 6, 30.5 cM) and GENE6 (chr 19, 42.1 cM). GENE1 data was used to fine-map the mutation for affection status, and GENE6 data for searching the Q1 mutation. All polymorphic sites (SNP loci) in the candidate gene sequences in replicate 2 were used (60 markers for GENE6, 282 for GENE1). For sampling, Q1 was first dichotomised by defining individuals with Q1 exceeding its top quartile as affected and the others as controls. In the linear regression phase, however, we used the true value of Q1 instead of the dichotomised class. Only one replicate was chosen here as to keep the sample size realistic and overall allelic heterogeneity lower. We sampled all the non-overlapping trios with one or two affected individuals from each pedigree, yielding 69 trios for Q1, and 83 for affection status. For GENE6 data, the search parameters were set to: maximal pattern length 10 markers and frequency threshold 5 occurrences. For GENE1 data, maximum length of a pattern was set to 8 markers and the frequency threshold for the patterns was set to 7. We also carried out the same experiments using lower frequency thresholds and longer patterns with similar results (not shown). One gap of one marker was allowed in the patterns to compensate for the missing data caused by haplotyping ambiguities that are more common with SNP markers than with the highly informative microsatellite markers used in the genome scans.

References

Bain S, Todd J, Barnett A (1990) The British Diabetic Association—Warren repository. Autoimmunity 7:83–85

Churchill G A, Doerge R W (1994) Empirical threshold values for quantitative trait mapping. Genetics 138:963–971

Devlin B, Risch N, Roeder K (1996) Disequilibrium mapping: composite likelihood for pairwise disequilibrium. Genomics 36:1–16

Kruglyak L (1999) Prospects for whole-genome linkage disequilibrium mapping of common disease genes. Nat Genet 22:139–144

Kruglyak L, Daly M J, Reeve-Daly M P, Lander E S (1996) Parametric and nonparametric linkage analysis: a unified multipoint approach. Am J Hum Genet 58:1347–1363

Lazzeroni L C (1998) Linkage disequilibrium and gene mapping: an empirical least-squares approach. Am J Hum Genet 62:159–170

Mannila H, Toivonen H T T (1997) Levelwise search and borders of theories in knowledge discovery. Data Mining and Knowledge Discovery 1(3): 241–258

McPeek M S, Strahs A (1999) Assessment of linkage disequilibrium by the decay of haplotype sharing, with application to fine-scale genetic mapping. Am J Hum Genet 65:858–875

Service S K, Temple Lang D W, Freimer N B, Sandkuijl L A (1999) Linkage-disequilibrium mapping of disease genes by reconstruction of ancestral haplotypes in founder populations. Am J Hum Genet 64:1728–1738

Spielman, R S, McGinnish R E, Ewens, W J (1993) Transmission test for linkage disequilibrium: the insulin gene region and insulin-dependent diabetes mellitus (IDDM). Am J Hum Genet 52:506–515

Terwilliger J D (1995) A powerful likelihood method for the analysis of linkage disequilibrium between trait loci and one ore more polymorphic marker loci. Am J Hum Genet 56:777–787

What is claimed is:

1. A method for gene mapping to locate a gene associated with a certain phenotype from a dataset of chromosome and phenotype data by analyzing an association between phenotype and genetic markers $m_i$, comprising:

i) searching from said dataset for all marker patterns P that satisfy a pattern evaluation function e(P), wherein a: the marker patterns are expressions within said dataset comprising genetic markers and their alleles and zero or more of the following: individual covariates, environmental variables and auxiliary phenotypes; and b: the pattern evaluation function e(P) is a measure of the association between the marker pattern P and a phenotype being studied, ii) scoring each marker $m_i$ of the data with a marker score $s(m_i)$, which is a function of the set $S_i$ defined as the set of marker patterns overlapping the marker $m_i$ and satisfying the pattern evaluation function e as defined in step i), and iii) locating said gene to the marker $m_i$ having the best score $s(m_i)$, wherein the best score is the highest obtained score if said scoring function is designed to give higher scores closer to the gene, or the lowest obtained score if said scoring function is designed to give lower scores closer to the gene, or locating said gene to a chromosomal region containing a set of best scoring markers.

2. The method of claim 1, wherein the chromosome data consists of either haplotypes or genotypes.

3. The method of claim 2, wherein said haplotypes and genotypes contain flexible regions.

4. The method of claim 1, wherein a) the phenotype being studied is qualitative, and b) the pattern evaluation function e(P) has the form e(P)=true if and only if e'(P)>x, where e'(P) is the signed association measure $\chi^2$ and x is a user specified minimum value wherein said signed value of the $\chi^2$ is negative if the relative frequency of the halotype pattern among the control chromosomes is higher than that of the trait-associated chromosomes, and otherwise positive, and c) the score $s(m_i)$ of marker $m_i$ as the size of $S_i$, also called marker-wise pattern frequency of $m_i$ and denoted by $f(m_i)$.

5. The method of claim 1, wherein a) the pattern evaluation function e(P) has the form e(P)=true if and only if e'(P)>x, where e'(P) is the absolute frequency of pattern P in the data and x is a user-specified value, b) in order to derive the score $s(m_i)$, the p value (statistical significance) of each marker pattern P in determining the phenotype being studied is evaluated, and c) the score $s(m_i)$ is the distance between the observed p value distribution of patterns in $S_i$ and the uniform distribution, defined as average of $(p_i-q_i)\log(p_i/q_i)$ over all i=1 . . . n, where n is the number of haplotype patterns in $S_i$, $p_i$ is the ith smallest p value in $S_i$, and $q_i$ is the expectation of the ith smallest p value, if the p values were randomly drawn from the uniform distribution.

6. The method of claim 5, where the p value is computed using a linear model of form $Y=\beta_1X_1+ \ldots +\beta_kX_k+\alpha Z+\beta_0$, where the dependent variable Y is the phenotype being studied, $X_1$ through $X_k$ are covariates, and Z is a dummy variable for the occurrence of the haplotype pattern, and the coefficients $\alpha$ and $\beta^*$ are adjusted for best fit, and then the significance of Z as a covariate is assessed using a t test with the null hypothesis "$\alpha=0$".

7. The method of claim 1, further refining each score $s(m_i)$ by replacing it by the marker-wise p value of the score $s(m_i)$, where the statistical significance of $s(m_i)$ is measured against the null hypotheses that there is no gene effect.

8. The method of claim 1, wherein an area returned from a prediction of a gene location is contiguous or fragmented or a point.

9. A computer-readable data storage medium having computer-executable program code stored thereon operative to perform the method of claim 1 when executed on a computer.

10. A computer system having executable program code that performs the method of claim 1.

* * * * *